US006444429B1

United States Patent
Han et al.

(10) Patent No.: US 6,444,429 B1
(45) Date of Patent: Sep. 3, 2002

(54) **GENE CODING FOR DNA LIGASE OF HYPERTHERMOPHILIC BACTERIA *AQUIFEX PYROPHILUS* AND PROTEIN EXPRESSED THEREFROM**

(75) Inventors: Ye-Sun Han; Yeon-Gyu Yu, both of Seoul; Jae-Hwan Lim, Gwacheon, all of (KR)

(73) Assignee: Korea Institute of Science and Technology, Seoul (KR)

( * ) Notice: Subject to any disclaimer, the term of this patent is extended or adjusted under 35 U.S.C. 154(b) by 0 days.

(21) Appl. No.: 09/708,426

(22) Filed: Nov. 9, 2000

(30) Foreign Application Priority Data

Nov. 10, 1999 (KR) ........................................ 1999-49591

(51) Int. Cl.[7] ................................................ C12Q 1/68
(52) U.S. Cl. ........................ 435/6; 435/69.1; 435/91.1; 435/91.2; 530/350
(58) Field of Search ............................... 435/5, 6, 91.1, 435/91.2, 69.1; 530/350

(56) References Cited

PUBLICATIONS

Cloning, purification, and characterization of NAD–dependent DNA ligase from *A. pyrophilus*. GenBank Accession No. AF152998, Direct Submission, submitted May 1999.*
Michael W. W. Adams, Annu. Rev. Microbiol., vol. 47, pp. 627–658, "Enzymes and Proteins From Organisms That Grow Near and Above 100° C.", 1993 (pp. 630–631; 640–641 and 658 will be submitted later).
Hyun–Seock Shin, et al., J. Microbiol. Biotechnol., vol. 9, No. 4, pp. 404–413, "Random Sequence Analysis of the Genomic DNA Methanopyrus Kandleri and Melecular Cloning of the Gene Encoding a Homologue of the Catalytic Subunit of Carbon Monoxide Dehydrogenase", 1999.

Tomas Lindahl, et al., Annu. Rev. Biochem., pp. 251–279, "Mammalian DNA Ligases", 1992.

Jianying Luo, et al., Nucleic Acids Research, vol. 24, No. 15, pp. 3079–3085, "Identification of Essential Residues in Thermus Thermophilus DNA Ligase", 1996.

I.R. Lehman, Science, vol. 186, pp. 790–797, "DNA Ligase: Structure, Mechanism, and Function", Nov. 24, 1974.

Mats Nilsson, et al., Science, vol. 265, pp. 2085–2088, "Padlock Probes: Circularizing Oligonucleotides for Localized DNA Detection", Sep. 30, 1994.

Francis Barany, Proc. Natl. Acad. Sci. USA, vol. 88, pp. 189–193, "Genetic Disease Detection and DNA Amplification Using Cloned Thermostable Ligase", Jan. 1991.

\* cited by examiner

*Primary Examiner*—W. Gary Jones
*Assistant Examiner*—Janell E. Taylor
(74) *Attorney, Agent, or Firm*—Oblon, Spivak, McClelland, Maier & Neustadt, P.C.

(57) ABSTRACT

The present invention relates to a gene coding for a thermostable DNA ligase from *Aquifex pyrophilus*, a hyperthermophilic Bacterium, a protein having an amino acid sequence expressed therefrom and a probe used for detecting said ligase DNA. More particularly, the present invention is directed to a gene having a base sequence of SEQ. ID. NO: 3 and a thermostable DNA ligase having an amino acid sequence expressed therefrom (SEQ. ID. NO: 4).

Since *Aquifex pyrophilus* DNA ligase of the present invention has 75% of the ligation activity after heating at 95 ° C. for 1 hour, the ligase has higher stability than DNA ligases from the preexisting bacteria under high temperature and thus it can be advantageously used in genetic diseases assay of medical field, etc.

6 Claims, 12 Drawing Sheets

Figure 2

SEQUENCE LISTING

```
<160> NUMBER OF SEQ ID NOS: 12

<210> SEQ ID NO 1
<211> LENGTH: 39
<212> TYPE: DNA
<213> ORGANISM: Aquifex pyrophilus

<400> SEQUENCE: 1
gcctcacgtt cacatatgtt cacccccgaa agggaaagg                               39

<210> SEQ ID NO 2
<211> LENGTH: 45
<212> TYPE: DNA
<213> ORGANISM: Aquifex pyrophilus

<400> SEQUENCE: 2
gctaggcatg tcggatcctt aaaatagcct tcccatctta acctc                        45

<210> SEQ ID NO 3
<211> LENGTH: 2160
<212> TYPE: DNA
<213> ORGANISM: Aquifex pyrophilus
<220> FEATURE:
<221> NAME/KEY: CDS
<222> LOCATION: (1)..(2157)

<400> SEQUENCE: 3 atg ttc acc ccc gaa agg gaa agg gag ctt ata gaa aag acg agg gag     48
```

-continued

```
       Met Phe Thr Pro Glu Arg Glu Arg Glu Leu Ile Glu Lys Thr Arg Glu
       1               5                   10                  15 ctt tta gag cga ata aag agc ctt aaa gat tta agc ctt gag gaa gca        96
Leu Leu Glu Arg Ile Lys Ser Leu Lys Asp Leu Ser Leu Glu Glu Ala
                20                  25                  30 aaa agg ctt gcg gaa gaa ctg aaa gaa gtt atc agg ttt cac gac tac       144
Lys Arg Leu Ala Glu Glu Leu Lys Glu Val Ile Arg Phe His Asp Tyr
            35                  40                  45 aag tat tac gtt cag gca agt ccc gta ata agc gat tac gac tat gac       192
Lys Tyr Tyr Val Gln Ala Ser Pro Val Ile Ser Asp Tyr Asp Tyr Asp
        50                  55                  60 aga tta ttc agg gct ctg aag gag ata gag cgg aag ttt ccc cag ctt       240
Arg Leu Phe Arg Ala Leu Lys Glu Ile Glu Arg Lys Phe Pro Gln Leu
65                  70                  75                  80 ata act ccc gac tcc ccc acc cag agg gtt gcg agc gag ata acg gga       288
Ile Thr Pro Asp Ser Pro Thr Gln Arg Val Ala Ser Glu Ile Thr Gly
                85                  90                  95 gag ttc cca acg gta aag cac tac gca ccc atg ctc tcc ctt gat aat       336
Glu Phe Pro Thr Val Lys His Tyr Ala Pro Met Leu Ser Leu Asp Asn
            100                 105                 110 gcc tac acc gag gag gag ctc aaa gag tgg gac aga agg gta agg gag       384
Ala Tyr Thr Glu Glu Glu Leu Lys Glu Trp Asp Arg Arg Val Arg Glu
        115                 120                 125 ctt acc ggt ttt gag gtt gtt gag tat acg gtt gaa ccg aag ctt gac       432
Leu Thr Gly Phe Glu Val Val Glu Tyr Thr Val Glu Pro Lys Leu Asp
130                 135                 140 ggt gcg ggc ata gct ctc gtt tat aag gac gat att ttc gta agg gga       480
Gly Ala Gly Ile Ala Leu Val Tyr Lys Asp Asp Ile Phe Val Arg Gly
                150                 155                 160
145 gcg acg agg gga gac ggg gaa tac gga gaa gac att acc aac aac ctg       528
Ala Thr Arg Gly Asp Gly Glu Tyr Gly Glu Asp Ile Thr Asn Asn Leu
            165                 170                 175 aag acg ata aaa aca ata cct tta aag gcg gaa ttt tca agg ttc ggg       576
Lys Thr Ile Lys Thr Ile Pro Leu Lys Ala Glu Phe Ser Arg Phe Gly
        180                 185                 190 ata aag ctg gcg gag att agg gga gag gta gtt ata aat aag gag gag       624
Ile Lys Leu Ala Glu Ile Arg Gly Glu Val Val Ile Asn Lys Glu Glu
                195                 200                 205 ttt aaa aag ctc aat cag gaa agg ata gag gag gga ctt ccc ccc ttt       672
Phe Lys Lys Leu Asn Gln Glu Arg Ile Glu Glu Gly Leu Pro Pro Phe
            210                 215                 220 gca aat ccc aga aac gct gca gcc ggc tca ata agg cag aag gac ccg       720
Ala Asn Pro Arg Asn Ala Ala Ala Gly Ser Ile Arg Gln Lys Asp Pro
225                 230                 235                 240 aaa gaa gtt gca aag aga agg ctc gag gcg gta gtt tat cag ctc tca       768
Lys Glu Val Ala Lys Arg Arg Leu Glu Ala Val Val Tyr Gln Leu Ser
                245                 250                 255 tac gta gag cct cca gag agg gac cct aaa acc cac tac gaa tct ctt       816
Tyr Val Glu Pro Pro Glu Arg Asp Pro Lys Thr His Tyr Glu Ser Leu
            260                 265                 270 aaa atg ctt gat aca ctc ggt ttt aaa acc ctt ttt aag gat acg aag       864
Lys Met Leu Asp Thr Leu Gly Phe Lys Thr Leu Phe Lys Asp Thr Lys
        275                 280                 285 ctg tgc agg gga ata gat gag gta ata gag tat tgc aag gag tgg gaa       912
Leu Cys Arg Gly Ile Asp Glu Val Ile Glu Tyr Cys Lys Glu Trp Glu
    290                 295                 300 gag aaa aga gat acc tat ccc tac gag ata gac ggg atg gtc gtt aag       960
Glu Lys Arg Asp Thr Tyr Pro Tyr Glu Ile Asp Gly Met Val Val Lys
305                 310                 315                 320
```

```
                                              -continued gta aac gac aga agg ctt tac gag aaa ctt gga tac acc tca cac cac     1008
Val Asn Asp Arg Arg Leu Tyr Glu Lys Leu Gly Tyr Thr Ser His His
                325                 330                 335 ccg agg tgg gct ata gcc tac aag ttc aaa ccg aga agg gcg gta aca     1056
Pro Arg Trp Ala Ile Ala Tyr Lys Phe Lys Pro Arg Arg Ala Val Thr
            340                 345                 350 cag ctc gtt gat gtt gtt ttc cag gtt gga agg acg gga gcg att aca     1104
Gln Leu Val Asp Val Val Phe Gln Val Gly Arg Thr Gly Ala Ile Thr
        355                 360                 365 ccc gtt ggg aag ctt gaa ccc gtt cag gtt gga ggc gtt acg gta tct     1152
Pro Val Gly Lys Leu Glu Pro Val Gln Val Gly Gly Val Thr Val Ser
    370                 375                 380 tcc gtt tcc ctc ttt aac gaa gac ttt ata agg gag aag gat ata aga     1200
Ser Val Ser Leu Phe Asn Glu Asp Phe Ile Arg Glu Lys Asp Ile Arg
385                 390                 395                 400 atc ggg gac tac gtt ctc gtt gag agg gcg gga gac gta ata cct tac     1248
Ile Gly Asp Tyr Val Leu Val Glu Arg Ala Gly Asp Val Ile Pro Tyr
                405                 410                 415 ata gcg gac gtt tta aag gaa aag aga agc ggg gaa gaa agg gag ata     1296
Ile Ala Asp Val Leu Lys Glu Lys Arg Ser Gly Glu Glu Arg Glu Ile
            420                 425                 430 gta ttt ccc gaa agg tgt ccc tcc tgc ggt tct gag ctc gtg aag ctt     1344
Val Phe Pro Glu Arg Cys Pro Ser Cys Gly Ser Glu Leu Val Lys Leu
        435                 440                 445 ccc gac gaa gtg gca agg agg tgc ata aac ata ggt tgc ccc gcc cag     1392
Pro Asp Glu Val Ala Arg Arg Cys Ile Asn Ile Gly Cys Pro Ala Gln
    450                 455                 460 tcc gtt ttg agg gta aag cac tgg gca agc agg gaa gct atg gac ata     1440
Ser Val Leu Arg Val Lys His Trp Ala Ser Arg Glu Ala Met Asp Ile
465                 470                 475                 480 aga ggt ctc ggt gat gcg acg gta aag ctc ctc ttc aac agg gga ctc     1488
Arg Gly Leu Gly Asp Ala Thr Val Lys Leu Leu Phe Asn Arg Gly Leu
                485                 490                 495 gtg agg gac gtc ggg gac ctt tac tat ctg aag ctc ctt gac ctc ctc     1536
Val Arg Asp Val Gly Asp Leu Tyr Tyr Leu Lys Leu Leu Asp Leu Leu
            500                 505                 510 agg ctt ccg gga ttc ggt gaa agg tcc gcc tta aac ctt ctc agg gct     1584
Arg Leu Pro Gly Phe Gly Glu Arg Ser Ala Leu Asn Leu Leu Arg Ala
        515                 520                 525 ata gag gag agc aag aac aga ccc ata gat aga gtt ctt tac gga ctc     1632
Ile Glu Glu Ser Lys Asn Arg Pro Ile Asp Arg Val Leu Tyr Gly Leu
    530                 535                 540 gga ata agg tat gtt ggc tca acc acc gca aag aag ata tcc gag ata     1680
Gly Ile Arg Tyr Val Gly Ser Thr Thr Ala Lys Lys Ile Ser Glu Ile
545                 550                 555                 560 ata aac agc atc tgg gag ctt aaa gac ata ccc ata gag agg att atg     1728
Ile Asn Ser Ile Trp Glu Leu Lys Asp Ile Pro Ile Glu Arg Ile Met
                565                 570                 575 aga ctt gag ggt gtg gga tac aag gtt gcg aaa agt ata aag gag ttc     1776
Arg Leu Glu Gly Val Gly Tyr Lys Val Ala Lys Ser Ile Lys Glu Phe
            580                 585                 590 ttc tcc gtt ccc gaa aac ctt aag gtt ctt gag aag ctt gaa aaa gct     1824
Phe Ser Val Pro Glu Asn Leu Lys Val Leu Glu Lys Leu Glu Lys Ala
        595                 600                 605 ggt gta aac ctt gag aag aaa aaa acc gag aag ata gct gac gtt tta     1872
Gly Val Asn Leu Glu Lys Lys Lys Thr Glu Lys Ile Ala Asp Val Leu
    610                 615                 620 aag ggg aag acc ttt gtc ttt acg gga acc ctt gag tgc tgt tca agg     1920
Lys Gly Lys Thr Phe Val Phe Thr Gly Thr Leu Glu Cys Cys Ser Arg
625                 630                 635                 640
```

```
gag aag gct ggg gag ata gtt gag tcc ttg gga ggg aag ttc tca aac     1968
Glu Lys Ala Gly Glu Ile Val Glu Ser Leu Gly Gly Lys Phe Ser Asn
                645                 650                 655 agc gta acc tca aga acg gat tac ctc gtt gtg ggg aaa gag ccg gga     2016
Ser Val Thr Ser Arg Thr Asp Tyr Leu Val Val Gly Lys Glu Pro Gly
            660                 665                 670 agg acg aag ctt gaa aag gca aag aaa tac ggg gta aag acg att acc     2064
Arg Thr Lys Leu Glu Lys Ala Lys Lys Tyr Gly Val Lys Thr Ile Thr
        675                 680                 685 gag gaa gag ttt ata aac atg att aag gat tat gtt gac att gaa aag     2112
Glu Glu Glu Phe Ile Asn Met Ile Lys Asp Tyr Val Asp Ile Glu Lys
    690                 695                 700 tta aaa gaa gag aag aag aaa gag gtt aag atg gga agg cta ttt tga     2160
Leu Lys Glu Glu Lys Lys Lys Glu Val Lys Met Gly Arg Leu Phe
705                 710                 715
```

<210> SEQ ID NO 4
<211> LENGTH: 719
<212> TYPE: PRT
<213> ORGANISM: Aquifex pyrophilus

<400> SEQUENCE: 4

```
Met Phe Thr Pro Glu Arg Glu Arg Glu Leu Ile Glu Lys Thr Arg Glu
1               5                   10                  15

Leu Leu Glu Arg Ile Lys Ser Leu Lys Asp Leu Ser Leu Glu Glu Ala
            20                  25                  30

Lys Arg Leu Ala Glu Glu Leu Lys Glu Val Ile Arg Phe His Asp Tyr
        35                  40                  45

Lys Tyr Tyr Val Gln Ala Ser Pro Val Ile Ser Asp Tyr Asp Tyr Asp
    50                  55                  60

Arg Leu Phe Arg Ala Leu Lys Glu Ile Glu Arg Lys Phe Pro Gln Leu
65                  70                  75                  80

Ile Thr Pro Asp Ser Pro Thr Gln Arg Val Ala Ser Glu Ile Thr Gly
                85                  90                  95

Glu Phe Pro Thr Val Lys His Tyr Ala Pro Met Leu Ser Leu Asp Asn
            100                 105                 110

Ala Tyr Thr Glu Glu Glu Leu Lys Glu Trp Asp Arg Arg Val Arg Glu
        115                 120                 125

Leu Thr Gly Phe Glu Val Val Glu Tyr Thr Val Glu Pro Lys Leu Asp
    130                 135                 140

Gly Ala Gly Ile Ala Leu Val Tyr Lys Asp Asp Ile Phe Val Arg Gly
145                 150                 155                 160

Ala Thr Arg Gly Asp Gly Glu Tyr Gly Glu Asp Ile Thr Asn Asn Leu
                165                 170                 175

Lys Thr Ile Lys Thr Ile Pro Leu Lys Ala Glu Phe Ser Arg Phe Gly
            180                 185                 190

Ile Lys Leu Ala Glu Ile Arg Gly Glu Val Val Ile Asn Lys Glu Glu
        195                 200                 205

Phe Lys Lys Leu Asn Gln Glu Arg Ile Glu Glu Gly Leu Pro Pro Phe
    210                 215                 220

Ala Asn Pro Arg Asn Ala Ala Gly Ser Ile Arg Gln Lys Asp Pro
225                 230                 235                 240

Lys Glu Val Ala Lys Arg Arg Leu Glu Ala Val Val Tyr Gln Leu Ser
                245                 250                 255

Tyr Val Glu Pro Pro Glu Arg Asp Pro Lys Thr His Tyr Glu Ser Leu
            260                 265                 270
```

-continued

```
Lys Met Leu Asp Thr Leu Gly Phe Lys Thr Leu Phe Lys Asp Thr Lys
        275                 280                 285
Leu Cys Arg Gly Ile Asp Glu Val Ile Glu Tyr Cys Lys Glu Trp Glu
    290                 295                 300
Glu Lys Arg Asp Thr Tyr Pro Tyr Glu Ile Asp Gly Met Val Val Lys
305                 310                 315                 320
Val Asn Asp Arg Arg Leu Tyr Glu Lys Leu Gly Tyr Thr Ser His His
                325                 330                 335
Pro Arg Trp Ala Ile Ala Tyr Lys Phe Lys Pro Arg Arg Ala Val Thr
            340                 345                 350
Gln Leu Val Asp Val Val Phe Gln Val Gly Arg Thr Gly Ala Ile Thr
        355                 360                 365
Pro Val Gly Lys Leu Glu Pro Val Gln Val Gly Gly Val Thr Val Ser
    370                 375                 380
Ser Val Ser Leu Phe Asn Glu Asp Phe Ile Arg Glu Lys Asp Ile Arg
385                 390                 395                 400
Ile Gly Asp Tyr Val Leu Val Glu Arg Ala Gly Asp Val Ile Pro Tyr
                405                 410                 415
Ile Ala Asp Val Leu Lys Glu Lys Arg Ser Gly Glu Glu Arg Glu Ile
            420                 425                 430
Val Phe Pro Glu Arg Cys Pro Ser Cys Gly Ser Glu Leu Val Lys Leu
        435                 440                 445
Pro Asp Glu Val Ala Arg Arg Cys Ile Asn Ile Gly Cys Pro Ala Gln
    450                 455                 460
Ser Val Leu Arg Val Lys His Trp Ala Ser Arg Glu Ala Met Asp Ile
465                 470                 475                 480
Arg Gly Leu Gly Asp Ala Thr Val Lys Leu Leu Phe Asn Arg Gly Leu
                485                 490                 495
Val Arg Asp Val Gly Asp Leu Tyr Tyr Leu Lys Leu Leu Asp Leu Leu
            500                 505                 510
Arg Leu Pro Gly Phe Gly Glu Arg Ser Ala Leu Asn Leu Leu Arg Ala
        515                 520                 525
Ile Glu Glu Ser Lys Asn Arg Pro Ile Asp Arg Val Leu Tyr Gly Leu
    530                 535                 540
Gly Ile Arg Tyr Val Gly Ser Thr Thr Ala Lys Lys Ile Ser Glu Ile
545                 550                 555                 560
Ile Asn Ser Ile Trp Glu Leu Lys Asp Ile Pro Ile Glu Arg Ile Met
                565                 570                 575
Arg Leu Glu Gly Val Gly Tyr Lys Val Ala Lys Ser Ile Lys Glu Phe
            580                 585                 590
Phe Ser Val Pro Glu Asn Leu Lys Val Leu Glu Lys Leu Glu Lys Ala
        595                 600                 605
Gly Val Asn Leu Glu Lys Lys Thr Glu Lys Ile Ala Asp Val Leu
    610                 615                 620
Lys Gly Lys Thr Phe Val Phe Thr Gly Thr Leu Glu Cys Cys Ser Arg
625                 630                 635                 640
Glu Lys Ala Gly Glu Ile Val Glu Ser Leu Gly Gly Lys Phe Ser Asn
                645                 650                 655
Ser Val Thr Ser Arg Thr Asp Tyr Leu Val Val Gly Lys Glu Pro Gly
            660                 665                 670
Arg Thr Lys Leu Glu Lys Ala Lys Lys Tyr Gly Val Lys Thr Ile Thr
        675                 680                 685
```

```
Glu Glu Glu Phe Ile Asn Met Ile Lys Asp Tyr Val Asp Ile Glu Lys
        690                 695                 700
Leu Lys Glu Glu Lys Lys Glu Val Lys Met Gly Arg Leu Phe
705                 710                 715
```

<210> SEQ ID NO 5
<211> LENGTH: 31
<212> TYPE: DNA
<213> ORGANISM: Artificial
<220> FEATURE:
<223> OTHER INFORMATION: synthetic oligonucleotide

<400> SEQUENCE: 5
ggtaaagcaa tgggcaaaca gggaagctat g                          31

<210> SEQ ID NO 6
<211> LENGTH: 35
<212> TYPE: DNA
<213> ORGANISM: Artificial
<220> FEATURE:
<223> OTHER INFORMATION: synthetic oligonucleotide

<400> SEQUENCE: 6
gacataagag gtctcggtga tgacccagta aagct                      35

<210> SEQ ID NO 7
<211> LENGTH: 71
<212> TYPE: DNA
<213> ORGANISM: Artificial
<220> FEATURE:
<223> OTHER INFORMATION: synthetic oligonucleotide

<400> SEQUENCE: 7
ggagctttac tgggtcatca ccgagacctc ttatgtccat agcttccctg tttgcccatt    60
gctttaccct c                                                71

<210> SEQ ID NO 8
<211> LENGTH: 720
<212> TYPE: PRT
<213> ORGANISM: Aquifex aeolicus

<400> SEQUENCE: 8

```
Met Phe Thr Pro Glu Arg Glu Lys Glu Leu Gln Glu Lys Thr Arg Glu
1               5                   10                  15
Leu Leu Arg Lys Ile Lys Asp Val Lys Val Leu Ser Phe Glu Glu Ala
            20                  25                  30
Lys Lys Leu Ala Glu Asp Leu Arg Glu Val Ile Arg Tyr His Asp Tyr
        35                  40                  45
Lys Tyr Tyr Val Glu Ala Asn Pro Val Ile Pro Asp Tyr Asp Tyr Asp
    50                  55                  60
Arg Leu Phe Arg Ala Leu Lys Glu Ile Glu Lys Lys Tyr Pro Glu Leu
65                  70                  75                  80
Ile Thr Pro Asp Ser Pro Thr Gln Arg Val Ala Ser Glu Ile Ser Gly
                85                  90                  95
Glu Phe Pro Thr Val Lys His Tyr Thr Pro Met Leu Ser Leu Asp Asn
            100                 105                 110
Ala Tyr Ser Glu Asp Glu Leu Arg Glu Phe Asp Arg Arg Val Arg Gln
        115                 120                 125
Ile Thr Gly Leu Glu Val Val Gly Tyr Ala Val Glu Pro Lys Leu Asp
    130                 135                 140
```

-continued

```
Gly Ala Gly Ile Ala Leu Val Tyr Glu Asn Asp Leu Phe Val Arg Gly
145                 150                 155                 160

Ala Thr Arg Gly Asp Gly Glu Tyr Gly Glu Asp Ile Thr Asn Asn Leu
            165                 170                 175

Lys Thr Ile Lys Thr Ile Pro Leu Lys Ala Glu Phe Ser Arg Phe Gly
        180                 185                 190

Ile Lys Leu Ala Glu Ile Arg Gly Glu Val Val Ile Arg Lys Asp Glu
    195                 200                 205

Phe Gln Lys Leu Asn Lys Glu Arg Met Glu Glu Gly Leu Pro Pro Phe
210                 215                 220

Ala Asn Pro Arg Asn Ala Ala Gly Ser Ile Arg Gln Lys Asp Pro
225                 230                 235                 240

Lys Glu Val Ala Lys Arg Asn Leu Glu Ala Ile Val Tyr His Leu Ser
            245                 250                 255

Tyr Val Glu Pro Pro Glu Thr Glu Pro Pro Thr His Tyr Glu Ser Leu
        260                 265                 270

Lys Met Leu His Thr Leu Gly Phe Lys Thr Leu Phe Lys Asp Thr Lys
    275                 280                 285

Val Cys Lys Gly Ile Asp Glu Val Ile Glu Tyr Cys Lys Glu Trp Glu
290                 295                 300

Lys Lys Arg Asp Ser Tyr Pro Tyr Glu Ile Asp Gly Met Val Val Lys
305                 310                 315                 320

Val Asn Asp Arg Arg Leu Trp Lys Val Leu Gly Tyr Thr Ser His His
            325                 330                 335

Pro Arg Trp Ala Ile Ala Tyr Lys Phe Lys Pro Arg Arg Ala Val Thr
        340                 345                 350

Lys Leu Val Asp Val Val Phe Gln Val Gly Arg Thr Gly Thr Ile Thr
    355                 360                 365

Pro Val Gly Lys Leu Glu Pro Val Glu Leu Gly Gly Val Thr Val Ser
370                 375                 380

Ser Val Ser Leu Phe Asn Glu Asp Phe Ile Arg Glu Lys Asp Ile Arg
385                 390                 395                 400

Ile Gly Asp Trp Val Val Glu Arg Ala Gly Asp Val Ile Pro Tyr
            405                 410                 415

Val Val Glu Val Leu Lys Glu Lys Arg Thr Gly Glu Glu Lys Pro Val
        420                 425                 430

Glu Phe Pro Lys Tyr Cys Pro Ser Cys Gly Ser Glu Leu Val Lys Leu
    435                 440                 445

Pro Glu Glu Val Ala Ile Arg Cys Ile Asn Ile Ser Cys Pro Ala Gln
450                 455                 460

Ser Val Leu Arg Ile Lys His Trp Ala Ser Arg Asp Ala Met Asp Ile
465                 470                 475                 480

Arg Gly Leu Gly Asp Ala Thr Ile Lys Leu Leu Phe Asn Arg Gly Leu
            485                 490                 495

Ala Lys Asp Val Gly Asp Leu Tyr Tyr Leu Lys Leu Thr Asp Ile Leu
        500                 505                 510

Lys Leu Pro Gly Phe Gly Glu Lys Ser Ala Met Asn Leu Leu Lys Ala
    515                 520                 525

Ile Glu Glu Ser Lys Asn Arg Pro Leu Asp Arg Val Leu Tyr Gly Leu
530                 535                 540

Gly Ile Arg Tyr Val Gly Gln Thr Thr Ala Lys Lys Ile Ala Glu Ile
545                 550                 555                 560

Ile Asn Ser Val Trp Asp Leu Lys Asp Ile Pro Leu Glu Lys Leu Met
```

|       |       |       |       | 565   |       |       |       |       | 570   |       |       |       |       | 575   |       |
|-------|-------|-------|-------|-------|-------|-------|-------|-------|-------|-------|-------|-------|-------|-------|-------|

Arg Leu Glu Gly Ile Gly Tyr Lys Val Ala Arg Ser Ile Lys Glu Phe
            580                 585                 590

Phe Asn Ile Pro Gln Asn Leu Glu Val Leu Lys Leu Glu Lys Ala
            595                 600             605

Gly Val Asn Leu Ala Lys Lys Val Lys Glu Lys Val Ala Asp Val Leu
            610             615                 620

Lys Gly Lys Thr Phe Val Phe Thr Gly Thr Leu Asp Cys Cys Ser Arg
625                 630                 635                 640

Glu Lys Ala Gly Glu Ile Val Glu Met Leu Gly Gly Lys Phe Ser Asn
                645                 650                 655

Ser Val Thr Ser Lys Thr Asp Tyr Leu Val Val Gly Lys Asp Pro Gly
            660                 665                 670

Ala Thr Lys Leu Ser Lys Ala Lys Lys Tyr Gly Val Lys Thr Ile Thr
            675                 680                 685

Glu Glu Glu Phe Val Asn Met Ile Lys Asp Tyr Val Asp Leu Glu Lys
            690                 695                 700

Ile Lys Lys Glu Asp Lys Lys Glu Lys Pro Lys Ile Gly Arg Leu Phe
705                 710                 715                 720

<210> SEQ ID NO 9
<211> LENGTH: 712
<212> TYPE: PRT
<213> ORGANISM: Rhodothermus marinus

<400> SEQUENCE: 9

Met Glu Thr His Thr Ala Pro Gln Thr Ala Glu Ala Arg Leu Leu Glu
1               5                   10                  15

Ala Thr His Thr Leu Leu Gln Thr Val Arg Gln Arg Asp Leu Glu Ala
            20                  25                  30

Ile Asp Arg Lys Glu Ala Glu Ala Leu Ala Ala Arg Leu Arg Glu Val
            35                  40                  45

Leu Asn Gln His Ala Tyr Arg Tyr Tyr Val Leu Asp Asn Pro Leu Ile
            50                  55                  60

Pro Asp Ala Asp Tyr Asp Leu Leu Met Gln Ala Leu Arg Lys Leu Glu
65                  70                  75                  80

Ala Arg Phe Pro Glu Leu Val Thr Pro Asp Ser Pro Thr Gln Arg Val
                85                  90                  95

Gly Gly Pro Pro Leu Gly Arg Phe Glu Lys Val Arg His Pro Glu Pro
            100                 105                 110

Leu Leu Ser Leu Asn Asn Ala Phe Gly Glu Glu Asp Val Arg Val Trp
            115                 120                 125

Tyr Glu Arg Cys Cys Arg Met Leu Ala Glu Arg Leu Gly Gln Pro Val
            130                 135                 140

Gln Pro Ala Val Thr Ala Glu Leu Lys Ile Asp Gly Leu Ala Met Ala
145                 150                 155                 160

Leu Thr Tyr Glu Asn Gly Val Leu Ser Val Gly Ala Thr Arg Gly Asp
                165                 170                 175

Gly Ile Glu Gly Glu Asn Val Thr Gln Asn Val Arg Thr Ile Pro Ala
            180                 185                 190

Ile Pro Leu Arg Ile Pro Val Asp Pro Ala Val Gly Pro Pro Pro Thr
            195                 200                 205

Arg Leu Glu Val Arg Gly Glu Val Tyr Met Arg Lys Arg Asp Phe Glu
            210                 215                 220

```
Arg Leu Asn Glu Gln Leu Gln Ala Arg Gly Glu Arg Pro Phe Ala Asn
225                 230                 235                 240

Pro Arg Asn Ala Ala Ala Gly Ser Val Arg Gln Leu Asn Pro Gln Val
                245                 250                 255

Thr Ala Leu Arg Pro Leu Ser Phe Phe Ala Tyr Gly Ile Gly Pro Val
                260                 265                 270

Glu Gly Ala Glu Val Pro Asp Ser Gln Tyr Glu Val Leu Gln Trp Leu
            275                 280                 285

Gly Arg Leu Gly Phe Pro Val Asn Glu His Ala Arg Arg Phe Glu His
        290                 295                 300

Leu Asp Asp Val Leu Glu Tyr Cys Arg Tyr Trp Thr Glu His Arg Asp
305                 310                 315                 320

Glu Leu Asp Tyr Glu Ile Asp Gly Val Val Leu Lys Ile Asp His Arg
                325                 330                 335

Pro Trp Gln Ala Leu Leu Gly Ala Ile Ser Asn Ala Pro Arg Trp Ala
                340                 345                 350

Val Ala Tyr Lys Phe Pro Ala Arg Glu Ala Ile Thr Arg Leu Leu Asp
            355                 360                 365

Ile Met Val Ser Val Gly Arg Thr Gly Val Val Lys Pro Val Ala Val
        370                 375                 380

Leu Glu Pro Val Glu Val Gly Val Thr Val Ser Gln Ala Thr Leu
385                 390                 395                 400

His Asn Glu Asp Tyr Val Arg Ser Arg Asp Ile Arg Ile Gly Asp Leu
                405                 410                 415

Val Val Val Ile Arg Ala Gly Asp Val Ile Pro Gln Val Val Arg Pro
            420                 425                 430

Val Val Glu Ala Arg Thr Gly Asn Glu Arg Pro Trp Arg Met Pro Glu
        435                 440                 445

Arg Cys Pro Ser Cys Gly Ser Gln Leu Val Arg Leu Pro Gly Glu Ala
    450                 455                 460

Asp Tyr Tyr Cys Val Ala Ser Asp Cys Pro Ala Gln Phe Val Arg Leu
465                 470                 475                 480

Leu Glu His Phe Ala Gly Arg Asp Ala Met Asp Ile Glu Gly Met Gly
                485                 490                 495

Ser Gln Val Ala Arg Gln Leu Ala Glu Ser Gly Leu Val Arg Pro Leu
            500                 505                 510

Ser Asp Leu Tyr Arg Leu Lys Leu Glu Asp Leu Leu Lys Leu Glu Gly
        515                 520                 525

Phe Ala Glu Thr Arg Ala Arg Asn Leu Leu Arg Ala Ile Glu Ala Ser
    530                 535                 540

Lys Gln Arg Pro Leu Ser Arg Leu Leu Phe Gly Leu Gly Ile Arg His
545                 550                 555                 560

Val Gly Lys Thr Thr Ala Glu Leu Leu Val Gln Arg Phe Ala Ser Ile
                565                 570                 575

Asp Glu Leu Ala Ala Ala Thr Ile Asp Glu Leu Ala Ala Leu Glu Gly
            580                 585                 590

Val Gly Pro Ile Thr Ala Glu Ser Ile Ala Asn Trp Phe Arg Val Glu
        595                 600                 605

Asp Asn Arg Arg Leu Ile Glu Glu Leu Lys Glu Leu Gly Val Asn Thr
    610                 615                 620

Gln Arg Leu Pro Glu Glu Ala Pro Ala Ala Glu Ser Pro Val Arg Gly
625                 630                 635                 640

Lys Thr Phe Val Leu Thr Gly Ala Leu Pro His Leu Thr Arg Lys Glu
```

-continued

```
                645                 650                 655
Ala Glu Glu Leu Ile Lys Arg Ala Gly Gly Arg Val Ala Ser Ser Val
                660                 665                 670

Ser Arg Asn Thr Asp Tyr Val Val Gly Glu Asn Pro Gly Ser Lys
                675                 680                 685

Tyr Asp Arg Ala Arg Gln Leu Gly Ile Pro Met Leu Asp Glu Asp Gly
            690                 695                 700

Leu Leu Arg Leu Leu Gly Met Lys
705                 710

<210> SEQ ID NO 10
<211> LENGTH: 676
<212> TYPE: PRT
<213> ORGANISM: Thermus aquaticus

<400> SEQUENCE: 10

Met Thr Leu Glu Glu Ala Arg Lys Arg Val Asn Glu Leu Arg Asp Leu
1               5                   10                  15

Ile Arg Tyr His Asn Tyr Arg Tyr Tyr Val Leu Ala Asp Pro Glu Ile
                20                  25                  30

Ser Asp Ala Glu Tyr Asp Arg Leu Leu Arg Glu Leu Lys Glu Leu Glu
            35                  40                  45

Glu Arg Phe Pro Glu Leu Lys Ser Pro Asp Ser Pro Thr Leu Gln Val
50                  55                  60

Gly Ala Arg Pro Leu Glu Ala Thr Phe Arg Pro Val Arg His Pro Thr
65                  70                  75                  80

Arg Met Tyr Ser Leu Asp Asn Ala Phe Asn Leu Asp Glu Leu Lys Ala
                85                  90                  95

Phe Glu Glu Arg Ile Glu Arg Ala Leu Gly Arg Lys Gly Pro Phe Ala
                100                 105                 110

Tyr Thr Val Glu His Lys Val Asp Gly Leu Ser Val Asn Leu Tyr Tyr
            115                 120                 125

Glu Glu Gly Val Leu Val Tyr Gly Ala Thr Arg Gly Asp Gly Glu Val
        130                 135                 140

Gly Glu Glu Val Thr Gln Asn Leu Leu Thr Ile Pro Thr Ile Pro Arg
145                 150                 155                 160

Arg Leu Lys Gly Val Pro Glu Arg Leu Glu Val Arg Gly Glu Val Tyr
                165                 170                 175

Met Pro Ile Glu Ala Phe Leu Arg Leu Asn Glu Glu Leu Glu Glu Arg
            180                 185                 190

Gly Glu Arg Ile Phe Lys Asn Pro Arg Asn Ala Ala Ala Gly Ser Leu
        195                 200                 205

Arg Gln Lys Asp Pro Arg Ile Thr Ala Lys Arg Gly Leu Arg Ala Thr
210                 215                 220

Phe Tyr Ala Leu Gly Leu Gly Leu Glu Glu Val Glu Arg Glu Gly Val
225                 230                 235                 240

Ala Thr Gln Phe Ala Leu Leu His Trp Leu Lys Glu Lys Gly Phe Pro
                245                 250                 255

Val Glu His Gly Tyr Ala Arg Ala Val Gly Ala Glu Gly Val Glu Ala
            260                 265                 270

Val Tyr Gln Asp Trp Leu Lys Lys Arg Arg Ala Leu Pro Phe Glu Ala
        275                 280                 285

Asp Gly Val Val Lys Leu Asp Glu Leu Ala Leu Trp Arg Glu Leu
290                 295                 300
```

-continued

```
Gly Tyr Thr Ala Arg Ala Pro Arg Phe Ala Ile Ala Tyr Lys Phe Pro
305                 310                 315                 320

Ala Glu Glu Lys Glu Thr Arg Leu Leu Asp Val Val Phe Gln Val Gly
                325                 330                 335

Arg Thr Gly Arg Val Thr Pro Val Gly Ile Leu Glu Pro Val Phe Leu
            340                 345                 350

Glu Gly Ser Glu Val Ser Arg Val Thr Leu His Asn Glu Ser Tyr Ile
        355                 360                 365

Glu Glu Leu Asp Ile Arg Ile Gly Asp Trp Val Leu His Lys Ala
370                 375                 380

Gly Gly Val Ile Pro Glu Val Leu Arg Val Leu Lys Glu Arg Arg Thr
385                 390                 395                 400

Gly Glu Glu Arg Pro Ile Arg Trp Pro Glu Thr Cys Pro Glu Cys Gly
                405                 410                 415

His Arg Leu Leu Lys Glu Gly Lys Val His Arg Cys Pro Asn Pro Leu
            420                 425                 430

Cys Pro Ala Lys Arg Phe Glu Ala Ile Arg His Phe Ala Ser Arg Lys
        435                 440                 445

Ala Met Asp Ile Gln Gly Leu Gly Glu Lys Leu Ile Glu Arg Leu Leu
450                 455                 460

Glu Lys Gly Leu Val Lys Asp Val Ala Asp Leu Tyr Arg Leu Arg Lys
465                 470                 475                 480

Glu Asp Leu Val Gly Leu Glu Arg Met Gly Glu Lys Ser Ala Gln Asn
                485                 490                 495

Leu Leu Arg Gln Ile Glu Glu Ser Lys Lys Arg Gly Leu Glu Arg Leu
            500                 505                 510

Leu Tyr Ala Leu Gly Leu Pro Gly Val Gly Glu Val Leu Ala Arg Asn
        515                 520                 525

Leu Ala Ala Arg Phe Gly Asn Met Asp Arg Leu Leu Glu Ala Ser Leu
530                 535                 540

Glu Glu Leu Leu Glu Val Glu Val Gly Glu Leu Thr Ala Arg Ala
545                 550                 555                 560

Ile Leu Glu Thr Leu Lys Asp Pro Ala Phe Arg Asp Leu Val Arg Arg
                565                 570                 575

Leu Lys Glu Ala Gly Val Glu Met Glu Ala Lys Glu Lys Gly Gly Glu
            580                 585                 590

Ala Leu Lys Gly Leu Thr Phe Val Ile Thr Gly Glu Leu Ser Arg Pro
        595                 600                 605

Arg Glu Glu Val Lys Ala Leu Leu Arg Arg Leu Gly Ala Lys Val Thr
610                 615                 620

Asp Ser Val Ser Arg Lys Thr Ser Tyr Leu Val Val Gly Glu Asn Pro
625                 630                 635                 640

Gly Ser Lys Leu Glu Lys Ala Arg Ala Leu Gly Val Pro Thr Leu Thr
                645                 650                 655

Glu Glu Glu Leu Tyr Arg Leu Leu Glu Ala Arg Thr Gly Lys Lys Ala
            660                 665                 670

Glu Glu Leu Val
        675
```

<210> SEQ ID NO 11
<211> LENGTH: 671
<212> TYPE: PRT
<213> ORGANISM: Escherichia coli

<400> SEQUENCE: 11

```
Met Glu Ser Ile Glu Gln Gln Leu Thr Glu Leu Arg Thr Thr Leu Arg
1               5                   10                  15
His His Glu Tyr Leu Tyr His Val Met Asp Ala Pro Glu Ile Pro Asp
            20                  25                  30
Ala Glu Tyr Asp Arg Leu Met Arg Glu Leu Arg Glu Leu Glu Thr Lys
            35                  40                  45
His Pro Glu Leu Ile Thr Pro Asp Ser Pro Thr Gln Arg Val Gly Ala
50                  55                      60
Ala Pro Leu Ala Arg Phe Ser Gln Ile Arg His Glu Val Pro Met Leu
65              70                      75                  80
Ser Leu Asp Asn Val Phe Asp Glu Glu Ser Phe Leu Ala Phe Asn Lys
                85                  90                  95
Arg Val Gln Asp Arg Leu Lys Asn Asn Glu Lys Val Thr Trp Cys Cys
                100                 105                 110
Glu Leu Lys Leu Asp Gly Leu Ala Val Ser Ile Leu Tyr Glu Asn Gly
            115                 120                 125
Val Leu Val Ser Ala Ala Thr Arg Gly Asp Gly Thr Thr Gly Glu Asp
    130                 135                 140
Ile Thr Ser Asn Val Arg Thr Ile Arg Ala Ile Pro Leu Lys Leu His
145                 150                 155                 160
Gly Glu Asn Ile Pro Ala Arg Leu Glu Val Arg Gly Glu Val Phe Leu
                165                 170                 175
Pro Gln Ala Gly Phe Glu Lys Ile Asn Glu Asp Ala Arg Arg Thr Gly
            180                 185                 190
Gly Lys Val Phe Ala Asn Pro Arg Asn Ala Ala Ala Gly Ser Leu Arg
        195                 200                 205
Gln Leu Asp Pro Arg Ile Thr Ala Lys Arg Pro Leu Thr Phe Phe Cys
210                 215                 220
Tyr Gly Val Gly Val Leu Glu Gly Gly Glu Leu Pro Asp Thr His Leu
225                 230                 235                 240
Gly Arg Leu Leu Gln Phe Lys Lys Trp Gly Leu Pro Val Ser Asp Arg
                245                 250                 255
Val Thr Leu Cys Glu Ser Ala Glu Glu Val Leu Ala Phe Tyr His Lys
            260                 265                 270
Val Glu Glu Asp Arg Pro Thr Leu Gly Phe Asp Ile Asp Gly Val Val
        275                 280                 285
Ile Lys Val Asn Ser Leu Ala Gln Gln Glu Gln Leu Gly Phe Val Ala
    290                 295                 300
Arg Ala Pro Arg Trp Ala Val Ala Phe Lys Phe Pro Ala Gln Glu Gln
305                 310                 315                 320
Met Thr Phe Val Arg Asp Val Glu Phe Gln Val Gly Arg Thr Gly Ala
                325                 330                 335
Ile Thr Pro Val Ala Arg Leu Glu Pro Val His Val Ala Gly Val Leu
            340                 345                 350
Val Ser Asn Ala Thr Leu His Asn Ala Asp Glu Ile Glu Arg Leu Gly
        355                 360                 365
Leu Arg Ile Gly Asp Lys Val Val Ile Arg Arg Ala Gly Asp Val Ile
    370                 375                 380
Pro Gln Val Val Asn Val Val Leu Ser Glu Arg Pro Glu Asp Thr Arg
385                 390                 395                 400
Glu Val Val Phe Pro Thr His Cys Pro Val Cys Gly Ser Asp Val Glu
                405                 410                 415
```

```
Arg Val Glu Gly Glu Ala Val Ala Arg Cys Thr Gly Gly Leu Ile Cys
            420                 425                 430

Gly Ala Gln Arg Lys Glu Ser Leu Lys His Phe Val Ser Arg Arg Ala
            435                 440                 445

Met Asp Val Asp Gly Met Gly Asp Lys Ile Ile Asp Gln Leu Val Glu
            450                 455                 460

Lys Glu Tyr Val His Thr Pro Ala Asp Leu Phe Lys Leu Thr Ala Gly
465                 470                 475                 480

Lys Leu Thr Gly Leu Glu Arg Met Gly Pro Lys Ser Ala Gln Asn Val
            485                 490                 495

Val Asn Ala Leu Glu Lys Ala Lys Glu Thr Thr Phe Ala Arg Phe Leu
            500                 505                 510

Tyr Ala Leu Gly Ile Arg Glu Val Gly Glu Ala Thr Ala Ala Gly Leu
            515                 520                 525

Ala Ala Tyr Phe Gly Thr Leu Glu Ala Leu Glu Ala Ala Ser Ile Glu
            530                 535                 540

Glu Leu Gln Lys Val Pro Asp Val Gly Ile Val Val Ala Ser His Val
545                 550                 555                 560

His Asn Phe Phe Ala Glu Ser Asn Arg Asn Val Ile Ser Glu Leu
            565                 570                 575

Leu Ala Glu Gly Val His Trp Pro Ala Pro Ile Val Ile Asn Ala Glu
            580                 585                 590

Glu Ile Asp Ser Pro Phe Ala Gly Lys Thr Val Val Leu Thr Gly Ser
            595                 600                 605

Leu Ser Gln Met Ser Arg Asp Asp Ala Lys Ala Arg Leu Val Glu Leu
            610                 615                 620

Gly Ala Lys Val Ala Gly Ser Val Ser Lys Lys Thr Asp Leu Val Ile
625                 630                 635                 640

Ala Gly Glu Ala Ala Gly Ser Lys Leu Ala Lys Ala Gln Glu Leu Gly
            645                 650                 655

Ile Glu Val Ile Asp Glu Ala Glu Met Leu Arg Leu Leu Gly Ser
            660                 665                 670

<210> SEQ ID NO 12
<211> LENGTH: 731
<212> TYPE: PRT
<213> ORGANISM: Zymomonas mobilis

<400> SEQUENCE: 12

Met Asn Ala Asp Ile Asp Leu Phe Ser Tyr Leu Asn Pro Glu Lys Gln
1               5                   10                  15

Asp Leu Ser Ala Leu Ala Pro Lys Asn Leu Ser Arg Glu Gln Ala Val
            20                  25                  30

Ile Glu Leu Glu Arg Leu Ala Lys Leu Ile Ser His Tyr Asp His Leu
            35                  40                  45

Tyr His Asp Lys Asp Asn Pro Ala Val Pro Asp Ser Glu Tyr Asp Ala
50                  55                  60

Leu Val Leu Arg Asn Arg Arg Ile Glu Gln Phe Pro Asp Leu Ile
65                  70                  75                  80

Arg Pro Asp Ser Pro Ser Lys Val Gly Ser Arg Pro Asn Ser Arg
            85                  90                  95

Leu Pro Lys Ile Ala His Arg Ala Met Leu Ser Leu Asp Asn Gly
            100                 105                 110

Phe Leu Asp Gln Asp Val Glu Asp Phe Leu Gly Arg Val Arg Arg Phe
            115                 120                 125
```

-continued

```
Phe Asn Leu Lys Glu Asn Gln Ala Val Ile Cys Thr Val Glu Pro Lys
    130                 135                 140
Ile Asp Gly Leu Ser Cys Ser Leu Arg Tyr Glu Lys Gly Ile Leu Thr
145                 150                 155                 160
Gln Ala Val Thr Arg Gly Asp Gly Val Ile Gly Glu Asp Val Thr Pro
                165                 170                 175
Asn Val Arg Val Ile Asp Asp Ile Pro Lys Thr Leu Lys Gly Asp Asn
            180                 185                 190
Trp Pro Glu Ile Ile Glu Ile Arg Gly Glu Val Tyr Met Ala Lys Ser
        195                 200                 205
Asp Phe Thr Ala Leu Asn Ala Arg Gln Thr Glu Glu Asn Lys Lys Leu
    210                 215                 220
Phe Ala Asn Pro Arg Asn Ala Ala Gly Ser Leu Arg Gln Leu Asp
225                 230                 235                 240
Pro Asn Ile Thr Ala Arg Arg Ser Leu Arg Phe Leu Ala His Gly Trp
                245                 250                 255
Gly Glu Ala Thr Ser Leu Pro Ala Asp Thr Gln Tyr Gly Met Met Lys
            260                 265                 270
Met Ile Glu Ser Tyr Gly Leu Ser Val Ser Asn Leu Leu Ala Arg Ala
        275                 280                 285
Asp Asp Ile Gly Gln Met Leu Asp Phe Tyr Gln Lys Ile Glu Ala Glu
    290                 295                 300
Arg Ala Asp Leu Asp Phe Asp Ile Asp Gly Val Val Tyr Lys Leu Asp
305                 310                 315                 320
Gln Leu Asp Trp Gln Gln Arg Phe Gly Phe Ser Ala Arg Ala Pro Arg
                325                 330                 335
Phe Ala Leu Ala His Lys Phe Pro Ala Glu Lys Ala Gln Thr Thr Leu
            340                 345                 350
Leu Asp Ile Glu Ile Gln Val Gly Arg Thr Gly Val Leu Thr Pro Val
        355                 360                 365
Ala Lys Leu Glu Pro Val Thr Val Gly Gly Val Val Val Ser Ser Ala
    370                 375                 380
Thr Leu His Asn Ser Asp Glu Ile Glu Arg Leu Gly Val Arg Pro Gly
385                 390                 395                 400
Asp Arg Val Leu Val Gln Arg Ala Gly Asp Val Ile Pro Gln Ile Val
                405                 410                 415
Glu Asn Leu Thr Pro Asp Val Asp Arg Pro Ile Trp His Phe Pro His
            420                 425                 430
Arg Cys Pro Val Cys Asp Ser Val Ala Arg Arg Glu Glu Gly Glu Val
        435                 440                 445
Ala Trp Arg Cys Thr Gly Gly Leu Ile Cys Pro Ala Gln Arg Val Glu
    450                 455                 460
Ala Leu Cys His Phe Val Ser Arg Thr Ala Phe Glu Ile Asp Gly Leu
465                 470                 475                 480
Gly Lys Ser His Ile Glu Ser Phe Phe Ala Asp Lys Leu Ile Glu Thr
                485                 490                 495
Pro Ala Asp Ile Phe Arg Leu Phe Gln Lys Arg Gln Leu Leu Ile Glu
            500                 505                 510
Arg Glu Gly Trp Gly Glu Leu Ser Val Asp Asn Leu Ile Ser Ala Ile
        515                 520                 525
Asp Lys Arg Arg Lys Val Pro Phe Asp Arg Phe Leu Phe Ala Leu Gly
    530                 535                 540
```

-continued

```
Ile Arg His Val Gly Ala Val Thr Ala Arg Asp Leu Ala Lys Ser Tyr
545                 550                 555                 560

Gln Thr Trp Asp Asn Phe Lys Ala Ala Ile Asp Glu Ala Ala His Leu
                565                 570                 575

Arg Thr Ile Leu Gln Pro Ser Ser Glu Glu Ser Glu Glu Lys Tyr Gln
                580                 585                 590

Lys Arg Val Asp Lys Glu Leu Ile Ser Phe Phe His Ile Pro Asn Met
            595                 600                 605

Gly Gly Lys Ile Ile Arg Ser Leu Leu Asp Phe Phe Ala Glu Thr His
        610                 615                 620

Asn Ser Asp Val Val Ser Asp Leu Leu Gln Glu Val Gln Ile Glu Pro
625                 630                 635                 640

Leu Tyr Phe Glu Leu Ala Ser Ser Pro Leu Ser Gly Lys Ile Ile Val
                645                 650                 655

Phe Thr Gly Ser Leu Gln Lys Ile Thr Arg Asp Glu Ala Lys Arg Gln
                660                 665                 670

Ala Glu Asn Leu Gly Ala Lys Val Ala Ser Ser Val Ser Lys Lys Thr
            675                 680                 685

Asn Leu Val Val Ala Gly Glu Ala Ala Gly Ser Lys Leu Ser Lys Ala
        690                 695                 700

Lys Glu Leu Asp Ile Ser Ile Ile Asp Glu Asp Arg Trp His Arg Ile
705                 710                 715                 720

Val Glu Asn Gly Gly Gln Glu Ser Ile Lys Ile
                725                 730
```

GENE CODING FOR DNA LIGASE OF HYPERTHERMOPHILIC BACTERIA *AQUIFEX PYROPHILUS* AND PROTEIN EXPRESSED THEREFROM

BACKGROUND OF THE INVENTION

1. Field of the Invention

The present invention relates to a gene coding for a thermostable DNA ligase from *Aquifex pyrophilus*, a hyperthermophilic Bacterium, a protein having an amino acid sequence expressed therefrom and a probe used for detecting said ligase DNA. More particularly, the present invention is directed to a gene having a base sequence of SEQ. ID. NO: 3 and a thermostable DNA ligase having an amino acid sequence expressed therefrom (SEQ. ID. NO: 4).

2. Description of the Prior Art

Recently, attempts have been made to develop an enzyme in a microorganism growing in a special environment or to improve an existing enzyme so as to maintain its activity even in a special environment. Specifically, a microorganism capable of growing at a temperature near or above 100° C., the boiling point of water, was reported and an enzyme isolated from such an organism has been known to be able to maintain its activity without any degeneration at high temperatures near 100° C. Therefore, an effort has been made to screen an industrially applied enzyme that is used at high temperatures from such a microorganism.

Microorganisms that grow at such a high temperature are referred to collectively as hyperthermophile. They have an optimum growing temperature of above 80° C. and a type which grows at a temperature of above 115° C. among them was reported (M. W. W. Adams, Annu. Rev. Microbiol. 47:627–658, 1993). So far, hyperthermophiles of more than about 50 to 60 types were reported and they are found primarily in hot marine sediments. Most hyperthermophiles are classified as a type of primitive bacteria or archaea, and thermotoga and aquifex are known as bacteria belonging to hyperthermophiles.

*Aquifex pyrophilus* belonging to eubacteria represents the deepest branching with the Bacteria in assay results due to comparison of 16s RNA sequence and was known as autotrophic bacteria, which obtains energy by oxidizing or reducing sulphur (Huber R. et al., Syst. Appl. Microbiol. 15: 349–351, 1992). *Aquifex pyrophilus* is a hyperthermophilic marine bacterium that grows at a temperature between 67° C.–95° C., with an optimum growing temperature of 85° C. DNA ligase is an essential enzyme for a number of important cellular processes, including repair, replication and recombination of DNA in a cell since it catalyzes the formation of phosphodiester bonds at single-strand breaks in double-stranded DNA (Lehman I. R. Science, 186; 790–797, 1974, Lindahl, T. and Barnes, Annu. Rev. Biochem., 61: 251–281, 1992).

DNA ligase is present in all organisms, but its size, amino acid sequence and characteristics are very varied. DNA ligase is classified primarily into two types. One uses ATP as a cofactor and the other uses $NAD^+$. All DNA ligases from eukaryotes and viruses require ATP, and sizes of DNA ligases range from 103 kDa for the human DNA ligase I to 41 kDa for the bacteriophage T7 enzyme. Eubacterial DNA ligases require AND+according to the facts that have been elucidated so far. Among the amino acid sequences of several bacterial DNA ligases that have been identified (Ishino, Y., et al., Mol. & Gen. Genet. 204: 1–7, 1986; and Barany, F., and Gelfand, D. H. Gene (Amst.) 109, 1–11, 1991), DNA ligases using $NAD^+$ as a cofactor are proteins of monomer form with a size of 70–80 kDa, show a high level of sequence homology between them and have little similarity to DNA ligases requiring ATP.

Thermostable DNA ligases are used as essential enzymes in various assays of genetic diseases. For example, mutations of a single base or specific base sequence can be detected by DNA ligase chain reaction (LCR), and genetic diseases caused by change of trinucleotide repeats can be detected by repeat expansion detection (RED). Useful applications of thermostable DNA ligases include the preparation of a primer that is capable of reading a sequence from six bases and the determination of the presence of localized DNA by circularizing oligodeoxynucleotide (Barany, F., Proc. Natl. Acad. Sci. USA 88, 189–193, 1991; and Nilsson, M., et al., Science 265; 2085–2088). Therefore, there is an increase in the demand to develop thermostable DNA ligases essential for a number of important cellular processes, including repair, replication and recombination of DNA.

BRIEF DESCRIPTION OF THE FIGURES

FIG. 2 shows a sequence of a gene and an amino acid of *Aquifex pyrophilus* (A.P.—*Aquifex pyrophilus* (SEQ ID NO:3); A.a.—*Aquifex aeolicus* (SEQ ID NO:8); R.m.—*Rhodothermus marinus* (SEQ ID NO:9); T.a.—*Thermus aquaticus* (SEQ ID NO:10); E.c.—*Escherichia coli* (SEQ ID NO:11); Z.m.—*Zymomonas mobilis* (SEQ ID NO:12)).

SUMMARY OF THE INVENTION

The object of the present invention is to provide gene coding for a thermostable DNA ligase from *Aquifex pyrophilus*, a hyperthermophilic Bacterium, a protein having amino acid sequence expressed therefrom and a probe used for detecting said ligase DNA. More particularly, the present invention is directed to a gene having the base sequence (SEQ. ID. NO: 3) shown in FIG. 2, and a thermostable DNA ligase having the amino acid sequence expressed therefrom (SEQ. ID. NO: 4).

DETAILED DESCRIPTION OF THE INVENTION

The object of the present invention is to provide gene coding for a thermostable DNA ligase isolated from a hyperthermophilic bacteria and thermostable DNA ligase produced by expressing the gene in the host cell.

The inventors have carried out an investigation to achieve the object and thus found that DNA ligase isolated from Aquifex pyrophilus can maintain a stable state, even in high temperatures, and thus, shows its activity.

That is, the present invention relates to a gene coding for thermostable DNA ligase from Aquifex pyrophilus, a hyperthermophilic bacterium, a protein having an amino acid sequence expressed therefrom and a probe used for detecting said ligase DNA.

More particularly, the present invention is directed to a gene having the base sequence (SEQ. ID. NO: 3) in FIG. 2, and a thermostable DNA ligase having an amino acid sequence expressed therefrom (SEQ. ID. NO: 4).

Thus, the present invention is for obtaining thermostable DNA ligase by cloning a DNA ligase gene from a type of hyperthermophilic bacteria, Aquifex pyrophilus to determine the base sequence of the gene and expressing the ligase from the gene.

Also, the present invention provides a process for preparing Aquifex pyrophilus DNA ligase, comprising the steps of:
 a step culture E. coli BL21(DE3)/pSJS1240-pLig;
 a step to induce an expression of DNA ligase by adding IPTG in culture; and
 a step to recover and purify the expressed DNA ligase.

A purified thermostable DNA ligases of Aquifex pyrophilus can be used in a ligase chain reaction (LCR), which is an assay of genetic diseases, to detect mutations of a single base or specific base sequence and can be used in repeat expansion detection (RED) that can detect trinucleotide repeats.

Figure 1:
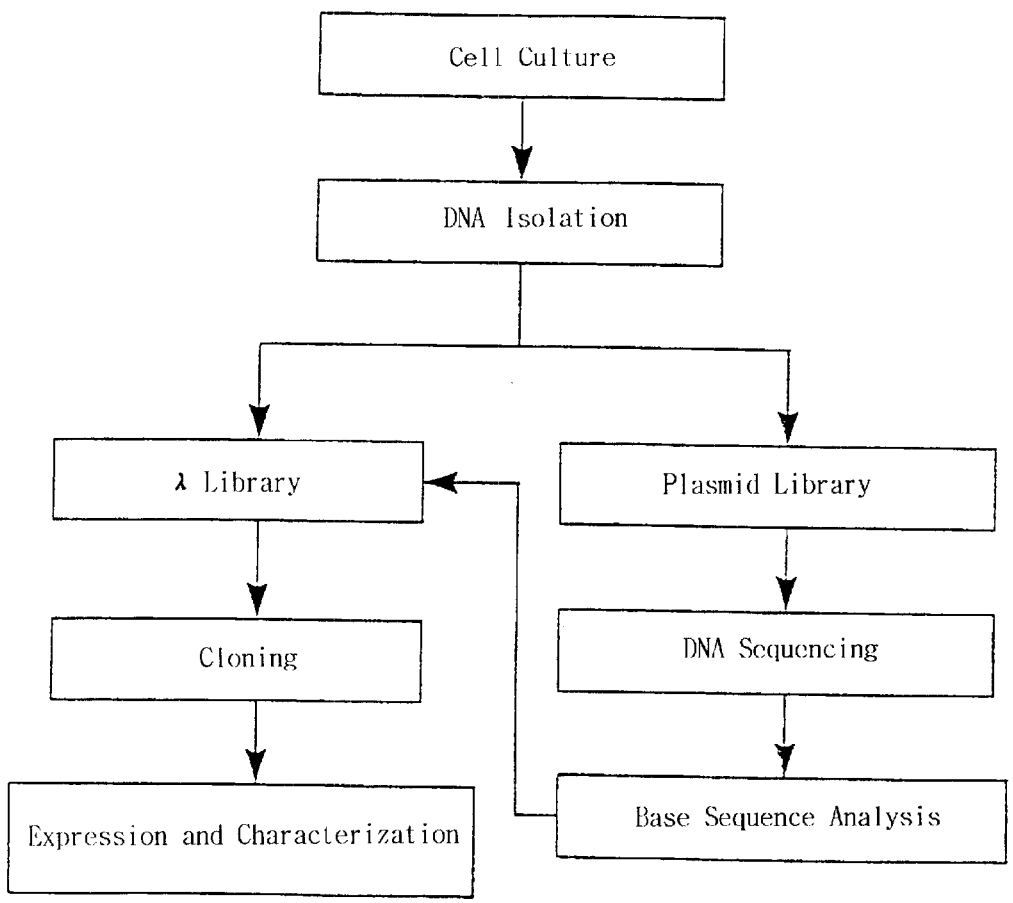
FIG. 1 shows a systematic diagram for a gene cloning that is used in the present invention.

The strain of Aquifex pyrophilus used in the present invention (Aquifex pyrophilus DSM #6858) can be obtained from DSM (Deutsche Sammlung von Mikroorganism und Zellkulturen Gmbh). After the microorganism is cultured (Huber, R. et al., Syst, Appl. Microbiolol, 15: 349–351, 1992), genome DNA is isolated from the microorganism and cloned as shown in FIG. 1.

A plasmid library and a genomic library of Aquifex pyrophilus are constructed by using pBluescript KS(+) plasmid and λ DASH II (Choi, I. G. et al., Extremophiles 1: 125–134, 1997). About 178 clones' sequences of the plasmid library are determined by a chain termination method, and then the BLAST (Basic Local Alignment Search Tool) programs are used to identify sequence similarity. One clone showing a high sequence homology with DNA ligase is used as a probe for screening genes of a genomic library to obtain a whole gene of DNA ligase by means of polymerase chain reaction (PCR).

Figure 2:
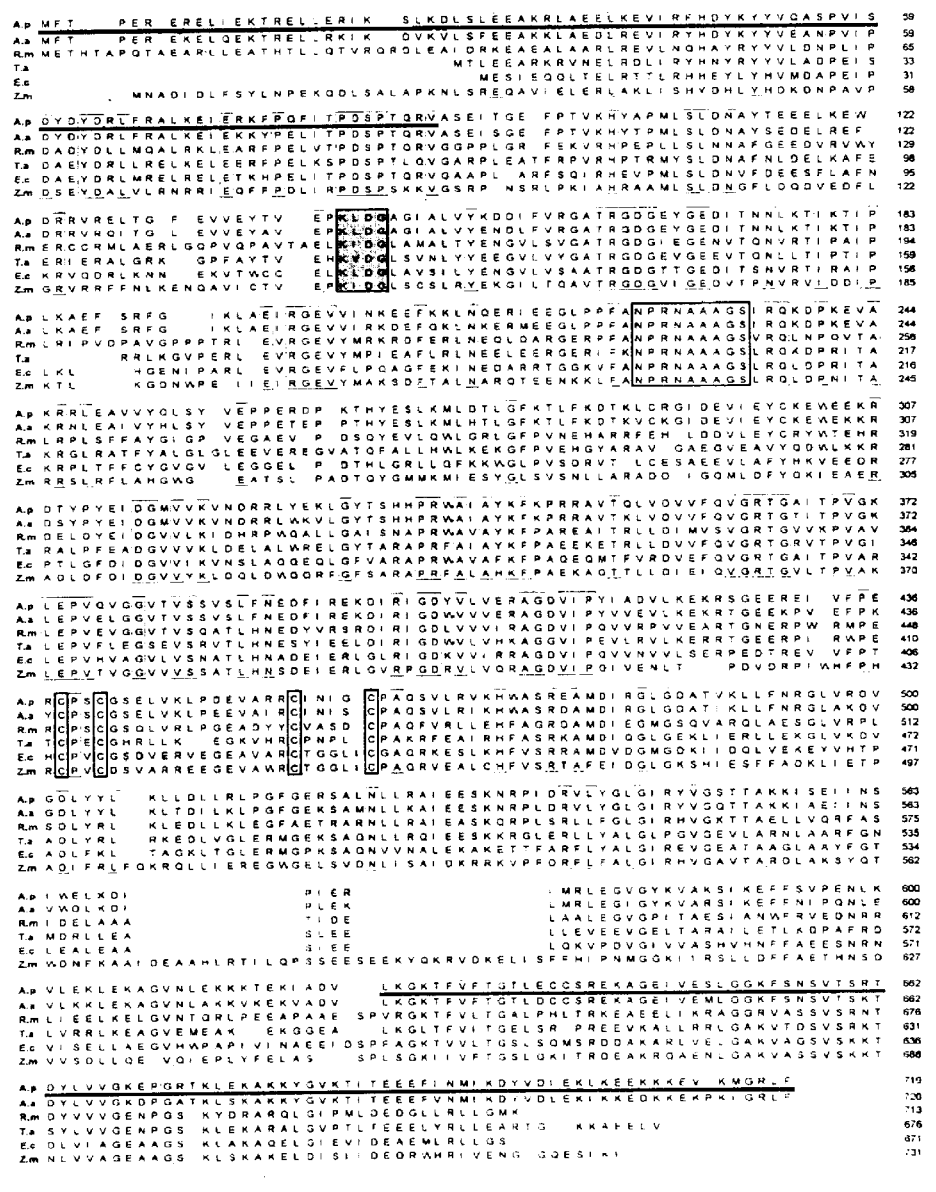

A genomic DNA library is selected by plaque hybridization screening using ECL-directed system (Amersham Co, Ohio, USA). DNA is finally extracted from three selected clones, cut with restriction enzyme HindIII and identified by southern blotting hybridization. After cloning by ligating into pBluescript KS(+), the sequence of the gene is determined in both directions by a chain termination method using oligomers produced by BioSynthesis Inc. (Lewisville, Tex., USA) as primers (FIG. 2).

The identified gene sequence consists of 2157 bp, the starting codon is ATG and the stop codon is TAA. The amino acid sequence of Aquifex pyrophilus DNA ligase is compared with Aquifex aeolicus and Thermus aquaticus ligases using the SEQSEE program. The results show that the rate of similarity between Aquifex pyrophilus and Aquifex aeolicus and Thermus aquaticus is 84% and 44%, respectively.

Figure 3:
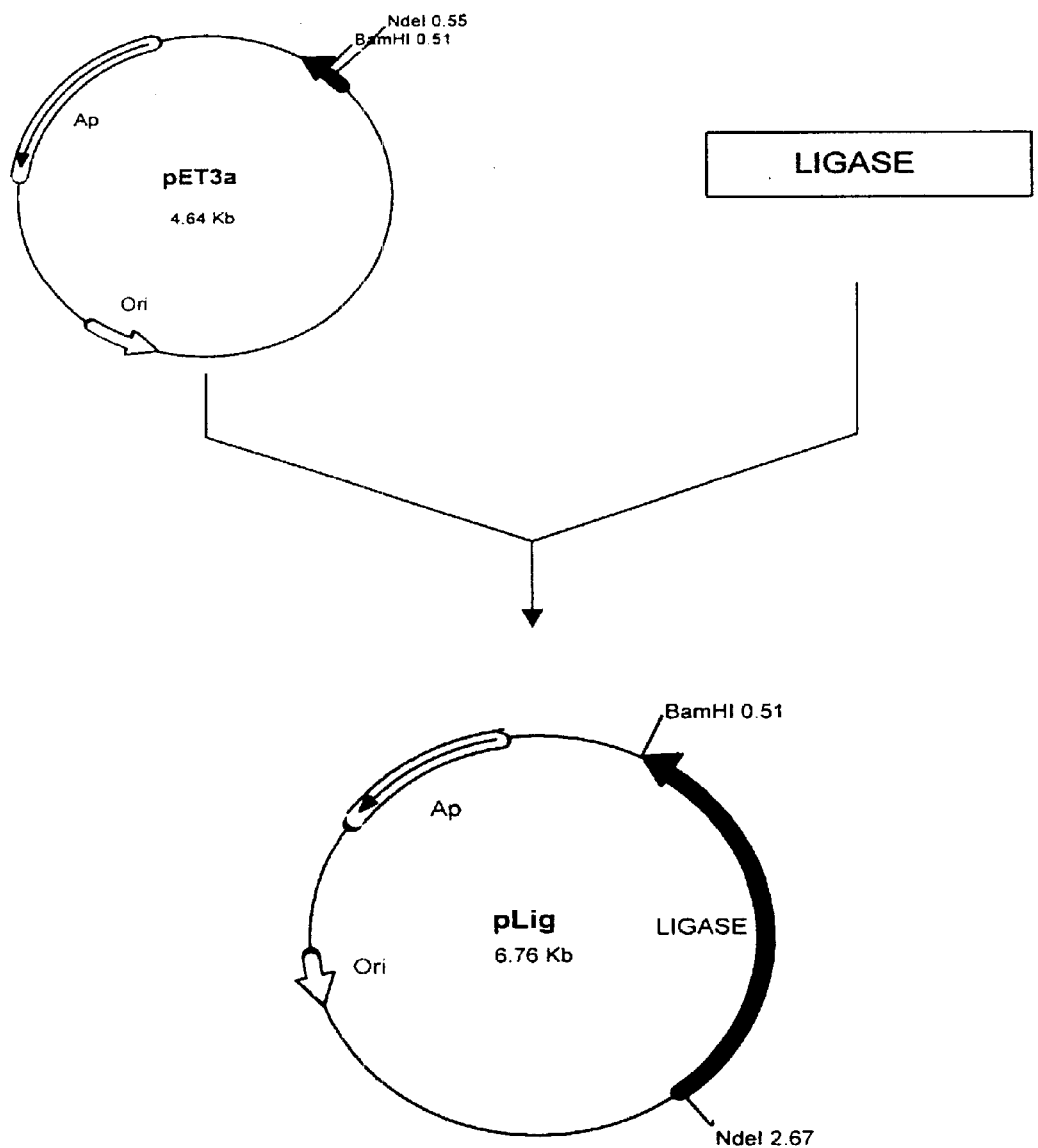
FIG. 3 shows a systemic diagram of the preparation of pLIG for overexpressing *Aquifex pyrophilus* DNA ligase.

For the expression of a recombinant DNA ligase, a clone containing the DNA ligase gene is subjected to PCR with two synthetic primers. The PCR product digested with NdeI and BamHI is isolated and ligated into a NdeI/BamHI digested pET3a vector (Novagen, Inc., Wis., USA) to prepare plasmid pLIG. The plasmid is transformed into E.coli BL21(DE3), which contains plasmid pSJS1240 (FIG. 3). An E.coli strain (E. coli BL21(DE3)/pSJS1240-pLig) containing pLIG was deposited in the Korean Collection for Type Cultures on Nov. 1, 1999 and assigned by accession No. KCTC 0686 BP. Plasmid pSJS1240 is prepared to express the rare tRNA genes for arginine (AGA) and isoleucine (ATA). The synthetic primer sequences that were used are as follows:
 LIG-F (SEQ. ID. NO: 1):
 5'-GCCTCACGTTCACATATGTTCACCC CCGAAAGGGAAAGG-3',
 LIG-R (SEQ. ID. NO: 2):
 5'-GCTAGGCATGTCGGATCCTTAAAATAGCC TTC-CCATCTTAACCTC -3'.

The several recombinant clones harboring the plasmid containing the DNA ligase gene are inoculated in the LB medium containing 100 μg/ml of ampicillin. The expression of DNA ligase is determined by SDS-PAGE. Among the clones, one recombinant clone showing strong expression of the ligase is selected. Production of the Aquifex pyrophilus DNA ligase protein is induced by the addition of isopropyl β-D-thiogalactopyranoside (IPTG) to recombinant E. coli and the ligase protein is separated and purified through FPLC (LKB Pharmacia) by sequential treatment of S-sepharose, heparin sepharose, HiTrap-Blue and Superdex S-200 columns. The purified proteins are taken from each purification step and subjected to electrophoresis on a 10% SDS-polyacrylamide gel (PAGE). As a result, proteins with a size of 82 kDa and 74 kDa are identified (FIG. 4).

Figure 4A:
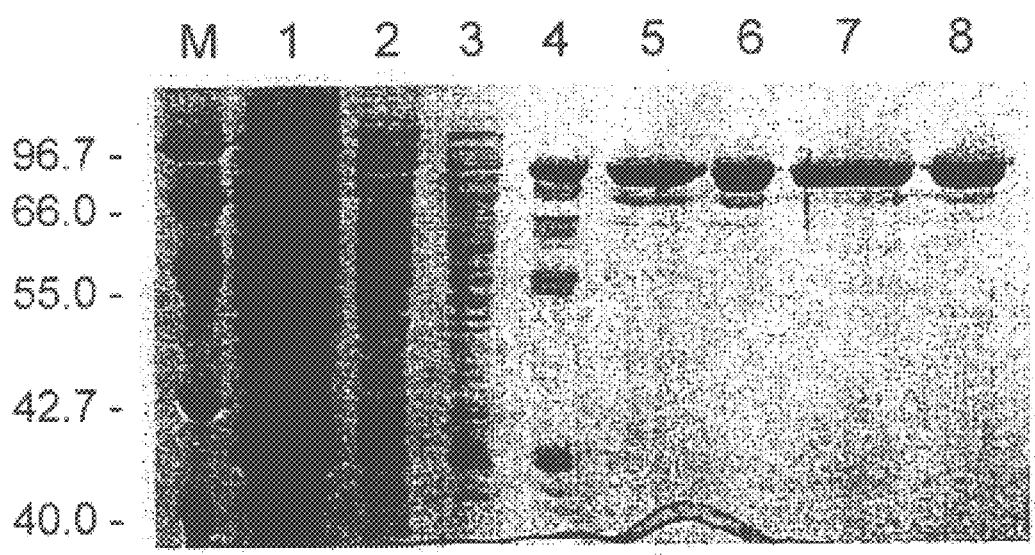
FIG. 4 is an autoradiogram showing the result of electrophoresis on an SDS polyacrylamide gel (12.5%) of a DNA ligase protein at each step of purification.

FIG. 4a shows the electrophoresis result of a DNA ligase protein on SDS polyacrylamide gel, wherein M is a standard-sized sample, Lane 1 is crude extract of uninduced cells, lane 2 is crude extract of induced cells, lane 3 is soluble fraction after centrifugation, lane 4 is a centrifuged soluble fraction after heat treatment, lane 5, 6, 7 and 8 are fractions containing DNA ligase separated from S-sepharose, Heparin-sepharose, HiTrap-Blue sepharose and Superdex-S200 chromatography, respectively.

Figure 4B:
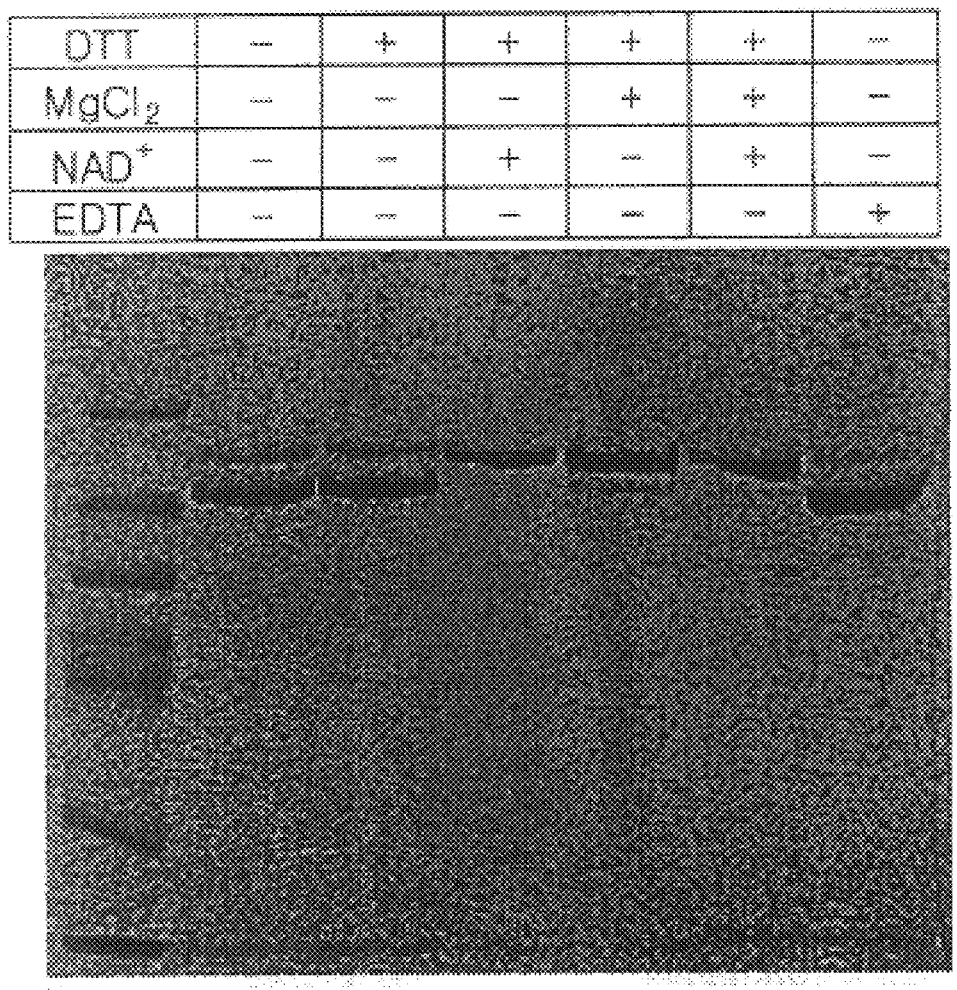

In FIG. 4b, the upper bands indicate the DNA ligase to which the adenyl group, which is part of a cofactor, is added; and the lower bands indicate the DNA ligase to which adenyl group is not bound. This is identified by SDS-PAGE analysis after $NAD^+$ or $MgCl_2$ is added directly to DNA ligase to react (Luo, J., and Barani, F., Nucleic Acids Research 24: 3079–3085, 1996).

The activity of the DNA ligase is assayed by using λ DNA digested with HindIII as a substrate containing a DNA fragment having an annealed end. The nick-closing activity of the DNA ligase is determined by using three synthetic oligonucleotides, as shown below:
 LA-1 (SEQ. ID. NO: 5):
 5 '-GGTAAAGCAATGGGCAAACAGGGAAGCTATG-3',
 LA-2 (SEQ. ID. NO: 6):
 5'-GACATAAGAGGTCTCGGTGATGACCCAGTAAA GCT-3',
 LA-3 (SEQ. ID. NO: 7):
 5'-GGAGCTTTACTGGGTCATCACCGAGACCTCTTA TGTCCATAGCTTCCCT GTTT GCCCATTGCTTTACCCTC-3'.

One of three oligonucleotides is radiolabeled with a radioactive isotope, and the samples are heated for 5 min at 95° C., chilled on ice and analyzed by electrophoresis on a 10% polyacrylamide gel containing 7M urea.

Figure 8:
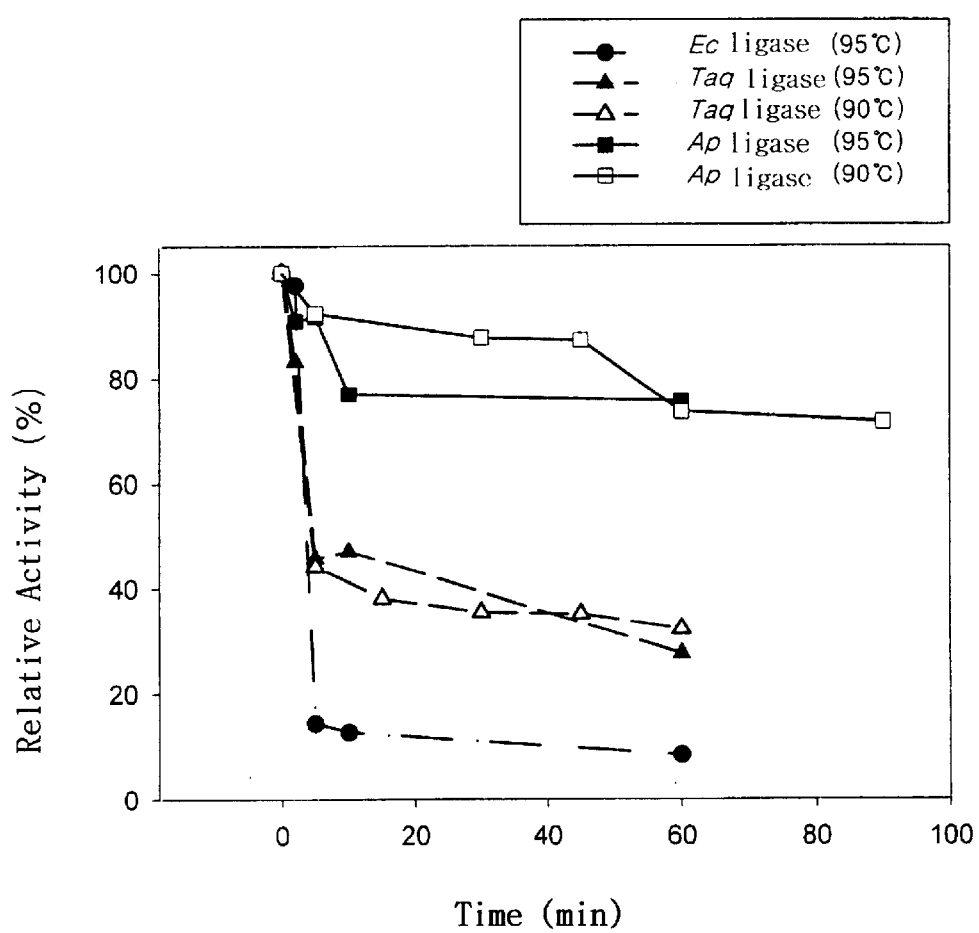
FIG. 8 is a graph showing a residual activity of DNA ligase after being heated.

To measure the thermostability of the DNA ligase, the DNA ligase of Aquifex pyrophilus is incubated in a buffer solution at 95° C. Aliquots are taken at regular time intervals, immediately chilled on ice and the residual activity of each aliquot is analyzed (FIG. 8). To compare the thermostability, the thermostability of *E. coli* DNA ligase and *Thermus aquifex* DNA ligase is also determined in the same manner as in *Aquifex pyrophilus*. In the case of *Aquifer pyrophilus* DNA ligase, more than 75% of the ligation activity remains after heating at 95 °C. for 1 hour while the half-lives of *E. coli* DNA ligase and *Thermus aquifer* DNA ligase are shown as 5 min and 2 min at 95° C., respectively. Therefore, it is understood that the *Aquifex pyrophilus* DNA ligase has a thermostability that is superior to the ligase from *E. coli* and *Thermus aquifex*.

Figure 9:
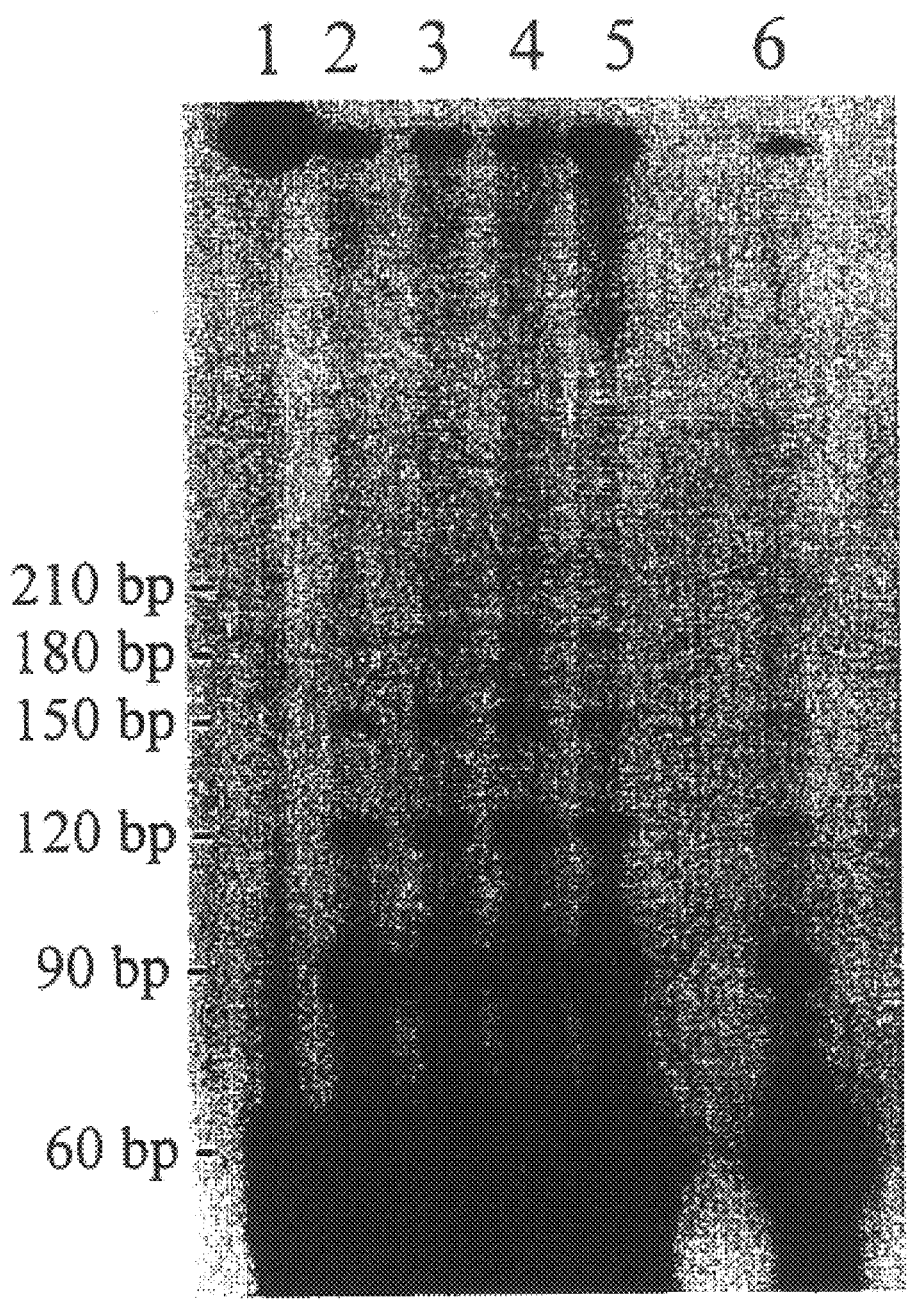
FIG. 9 is an autoradiogram showing the result of electrophoresis on acrylamide gel (10%), wherein the activity of *Aquifex pyrophilus* DNA ligase according to the invention is compared with that of Ampligase in RED.

The genetic diseases that are caused by a change of trinucleotide repeats in certain chromosome have been reported. To diagnose the diseases, repeat expansion detection (RED) assay using a thermostable ligase is currently utilized. In RED assay, Ampligase, which is commercially available by Epicentre, is generally used. In order to determine whether the DNA ligase of the present invention can be applied to RED, the activity of the DNA ligase according to the present invention was compared with that of Ampligase. As a result, it has been found that the DNA ligase of the present invention shows a higher activity than Ampligase so that the DNA ligase of the invention can be applied to RED more efficiently (FIG. 9).

DESCRIPTION OF THE PREFERRED EMBODIMENTS

The present invention is further described by the following examples but should not be construed as being limited by them.

EXAMPLE 1

Cloning of DNA Ligase Gene

To obtain a gene coding for DNA ligase, a systematic diagram for gene cloning as shown in FIG. 1 was established. A plasmid library was prepared from *Aquifex pyrophilus* as below.

After culturing *Aquifex pyrophilus* and obtaining a genomic DNA, the DNA was treated with a restriction enzyme HindIII and small gene fragments were prepared. These DNA were treated with HindIII and cloned to a linearized vector, pBluescript KS(+) so that 178 positive clones containing the *Aquifex pyrophilus* gene were selected. The selection method was a known α-complementation method, which is performed in media containing X-gal and IPTG. Base sequences of the clones were determined by the dideoxynucleotide chain termination method and one clone showing a high sequence homology with DNA ligase obtained from other species was obtained.

To obtain the inserted fragment containing a part of DNA ligase gene in the clone, PCR was performed (T7, KS primers; 95° C. 1 minute 30 seconds, 50° C. 1 minute, 72° C. 1 minute, 25 cycles). The synthetic fragment obtained above was used as a probe for screening genes in genomic library to obtain a whole DNA ligase gene. Further, a DNA fragment (=400 bp) was obtained by digestion of a clone containing a part of a DNA ligase gene with HindIII and EcoRV, and then separation on agarose gel. Said DNA fragment was then used as a probe to prepare a gene map of a whole DNA ligase gene obtained after screening.

A genomic library of *Aquifex pyrophilus* was constructed as follows: Genomic DNA was incompletely cut with HindIII to obtain appropriately sized (at least 10 bp) fragments. The fragments were ligated to HindIII-digested λ DASH II DNA (Stratagene, Calif., USA) and then packaged by using Gigapack XL packaging extract (Stratagene). Preparation of the genomic library was then completed by use of Sambrook's method (Sambrook, J., et al., Molecular cloning: a laboratory manual, $2^{nd}$ ed., Cold Spring Harbor Laboratory Press, Cold Spring Harbor, N. Y., 1989). The plaque forming unit of the prepared library was about $10^{10}$ pfu/ml.

To obtain a full length of a DNA ligase gene from the genomic library of *Aquifex pyrophilus*, plaque hybridization screening was carried out using the ECL-directed system (Amersham Co, Ohio, USA) with the above-obtained amplification fragment as a screening probe. Some of the clones that showed a positive signal were selected and confirmed by secondary screening. DNA was extracted from the selected clones and cut with restriction enzyme HindIII, and southern blotting hybridization was performed.

Fragments showing a positive signal were obtained by separation on agarose gel and ligated into pBluescript KS(+), which was previously linearized with HindIII. The base sequences of three prepared clones were determined by the dideoxynucleotide chain termination method using oligomers produced by Bio-Synthesis Inc. (Lewisville, Tex., USA) as primers (FIG. 2).

As a result, a DNA ligase gene of 2157 bp was identified. When the amino acid sequence of the *Aquifex pyrophilus* DNA ligase was compared with *Aquifex aeolicus* and *Thermus aquaticus* ligases, it was confirmed that the sequence shows a high sequence similarity with *Aquifex aeolicus* ligase (84%) and *Thermus aquaticus* ligase (44%).

EXAMPLE 2

Expression and Purification of DNA Ligase Protein

To express a DNA ligase protein in *E. coli*, of which the expression system is well established, the expression vector pET3a was linearized with NdeI and BamHI after the restriction enzyme map and the base sequence were examined. A clone containing a DNA ligase gene was amplified by PCR with two synthetic oligonucleotides and the gene fragment of 2,160 bp obtained by separation on agarose gel was digested with NdeI and BamHI. The digested fragments were then ligated into NdeI/BamHI digested pET3a vector (Novagen, Inc., Wis., USA) to prepare plasmid pLIG. The plasmid was transformed into *E.coli* BL21 (DE3) containing plasmid pSJS1240. Plasmid pSJS1240 was prepared to express the rare tRNA genes for arginine (AGA) and isoleucine (ATA). The used synthetic oligonucleotides were designed to include restriction sites of the used restriction enzymes and to be accurately ligated to the translation start site. The synthetic oligonucleotides sequences are as follows:

LIG-F (SEQ. ID. NO: 1):
5'-GCCTCACGTTCACATATGTTCACCC CCGAAAGGGAAAGG-3',

LIG-R (SEQ. ID. NO: 2):
5'-GCTAGGCATGTCGGATCCTTAAAATAGCC TTCCCATCTTAACCTC-3'.

*E.coli* BL21 (DE3)/pSJS1240, transformed with a specific DNA ligase gene, was inoculated in 1 liter of LB medium containing 100 µg/µl of ampicillin and 50 µg /µl of spectinomycin and grown until $OD_{600}$ becomes 0.8 at 30° C. Production of the *Aquifex pyrophilus* DNA ligase protein was then induced by the addition of isopropyl β-D-thiogalactopyranodide (IPTG) to the medium at a final concentration of 400 µM.

After incubation with shaking for 16 hours, the cells were harvested by centrifugation for 10 min at 4000×g. The obtained cells were resolved in 25 ml of dilution solution (50 mM Tris-HCl, pH7.5, 10 mM DTT, 10 mM $MgCl_2$, 0.1 mM phenylmethylsulfonyl fluoride) and then the freezing and thawing of the cells were repeated 3 times. The cells were lysed by French pressure cell (SLM instrument, Inc) at 8000 bars. The obtained cell extract was centrifuged for 1 hour at 25,000×g and the supernatant was heated at 80° C. for 30 min.

The sample was recentrifuged for 30 min at 25,000×g and the ligase proteins were purified from the supernatant through FPLC (LKB Pharmacia) by sequential treatment of S-sepharose, heparin-sepharose, HiTrap-Blue sepharose and Superdex S-200 columns. The purified proteins were subjected to electrophoresis on a 10% SDS-polyacrylamide gel (PAGE) and, as a result, proteins with a size of 82 kDa and 74 kDa were identified (FIG. 4).

In FIG. 4a showing the electrophoresis result of DNA ligase protein on SDS polyacrylamide gel, M is a standard-sized sample, lane 1 is a crude extract of uninduced cells, lane 2 is a crude extract of induced cells, lane 3 is a soluble fraction after centrifugation, lane 4 is centrifuged soluble fraction after heat treatment, lane 5, 6, 7 and 8 are fractions containing DNA ligase separated from S-sepharose, Heparin-sepharose, HiTrap-Blue sepharose and Superdex S-200 chromatography, respectively.

In FIG. 4b, the upper bands indicate the DNA ligase to which the adenyl group, which is part of a cofactor, is added; and the lower bands indicate the DNA ligase from which adenyl group leaves. This was identified by SDS-PAGE analysis after $NAD^+$, $MgCl_2$, or EDTA was added directly to DNA ligase solution to a concentration of 10 $\mu M$ to react for 30 minutes (Luo and Barani, Nucleic Acids Research 24: 3079–3085, 1996).

EXAMPLE 3

Determination of Activity of DNA Ligase Protein

The activity of the DNA ligase was assayed by using $\lambda$ DNA digested with HindIII as the DNA substrate containing an annealed end. The ligation reaction was performed in a 10 $\mu l$ reaction mixture containing 20 mM Tris-HCl, pH 7.5 or pH 8.0, 10 mM $MgCl_2$, 5 mM DTT, 5 mM AND+, 0.5 $\mu g$ HindIII-digested $\lambda$DNA, and the recombinant enzyme. The reactions were incubated at a constant temperature for 2 hr and stopped by adding 5 $\mu l$ stop/loading buffer (3×: 30% sucrose, 150 mM EDTA, 0.15% SDS and 0.03% bromophenol blue). All reaction solutions were subjected to electrophoresis in a 0.8% agarose gel at 60 V.

The nick-closing activity of the DNA ligase was determined by using as substrates three synthetic oligonucleotides, as shown below:

LA-1 (SEQ. ID. NO: 5):
5'-GGTAAAGCAATGGGCAAACAGGGAAGCTATG-3',

LA-2 (SEQ. ID. NO: 6):
5'-GACATAAGAGGTCTCGGTGATGACCCAGTAAAGCT-3',

LA-3 (SEQ. ID. NO: 7):
5'-GGAGCTTTACTGGGTCATCACCGAGACCTCTTA TGTCCATAGCTTCCCT GTTT GCCCATTGCTTTACCCTC-3'.

LA-2 in three oligonucleotides was radiolabeled with a radioactive isotope. For incorporating the isotope, 50 pmol of the gel-purified oligonucleotideLA-2 was reacted with 100 $\mu Ci$ of [$\gamma$-$^{32}$P]ATP (3000 Ci/mmol: Amersham Life Sciences, Buckinghamshire, UK) and 50U T4 polynucleotide kinase (Promega, Madison, Wis., USA) for 60 min at 37° C. After incubation for 10 min at 70° C. to remove the activity of T4 polynucleotide kinase, the unincorporated radiolabeled ATP was removed by centrifugation through Quick Spin Columns (Boehringer Mannheim, Germany).

The labeled oligonucleotide LA-2 and the other oligonucleotide LA-1 were annealed to the complimentary 71-mer of oligonucleotide LA-3 in an annealing buffer (50 mM Tris-HCl, pH 7.5, 200 mM NaCl) by heating at 90° C. for 2 min, followed by a gradual cooling to room temperature. The annealed oligonucleotide duplex was used as a substrate of the DNA ligase.

The annealed DNA substrate (500 fmol) was incubated with an amount of the DNA ligase in a 10 $\mu l$ reaction mixture (50 mM Tris-HCl, pH 8, 10 mM $MgCl_2$, 10 mM DTT, 5 mM $NAD^+$, 100 mM KCl and 0.1% Triton X-100) at 50° C. for 1 hour (Doherty, A. J and Ashford, S. R. 1996, Journal of biological Chemistry, 271: 11083–11089, 1996; and Shuman, S., and Schwer, B., Virology, 211: 73–83, 1995). After incubation, the reactions were terminated by adding a stop buffer (95% formamide, 1×TBE, 0.05% bromophenol blue, 0.05% Xylene cyanol and 0.2% SDS) followed by heating at 95° C. for 5 min. The reactants were chilled on ice and analyzed by electrophoresis on a 10% polyacrylamide gel containing 7 M urea in a TBE buffer (90 mM Tris-borate, 2.5 mM EDTA) at a constant power of 20 W. Gels were dried under vacuum after completion of electrophoresis and ligation products were visualized by autoradiography. For quantification of the product, the dried gel was scanned using a FUJIX BAS 1000 phosphoimager.

Figure 5:
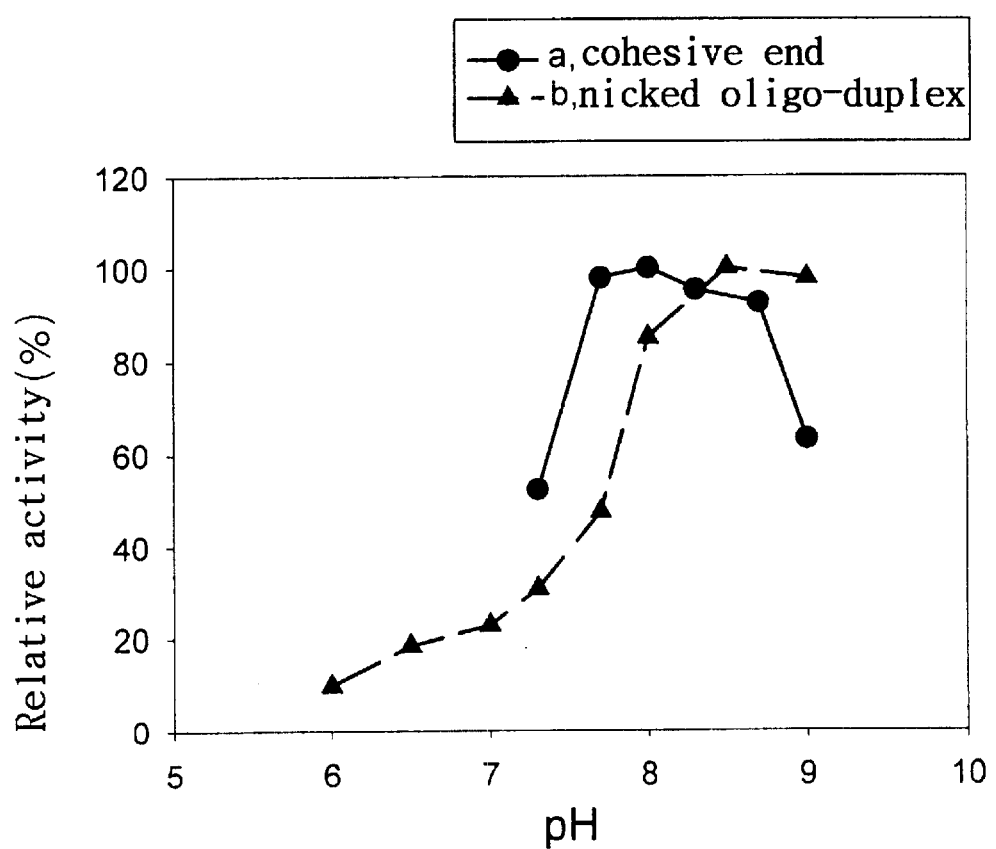
FIG. 5 is a graph showing DNA ligase activity according to pH changes in the reaction solution.

Activity of *Aquifex pyrophilus* DNA ligase was determined using, as a substrate, the annealed oligonucleotide duplex consisting of HindIII-cleaved $\lambda$ DNA fragments and synthetic 71mer oligonucleotide at various pH. As a result, it was confirmed that *Aquifex pyrophilus* DNA ligase shows highest activity when pH of Tris-HCl is 8.0 to 8.7 (FIG. 5).

Figure 6A:
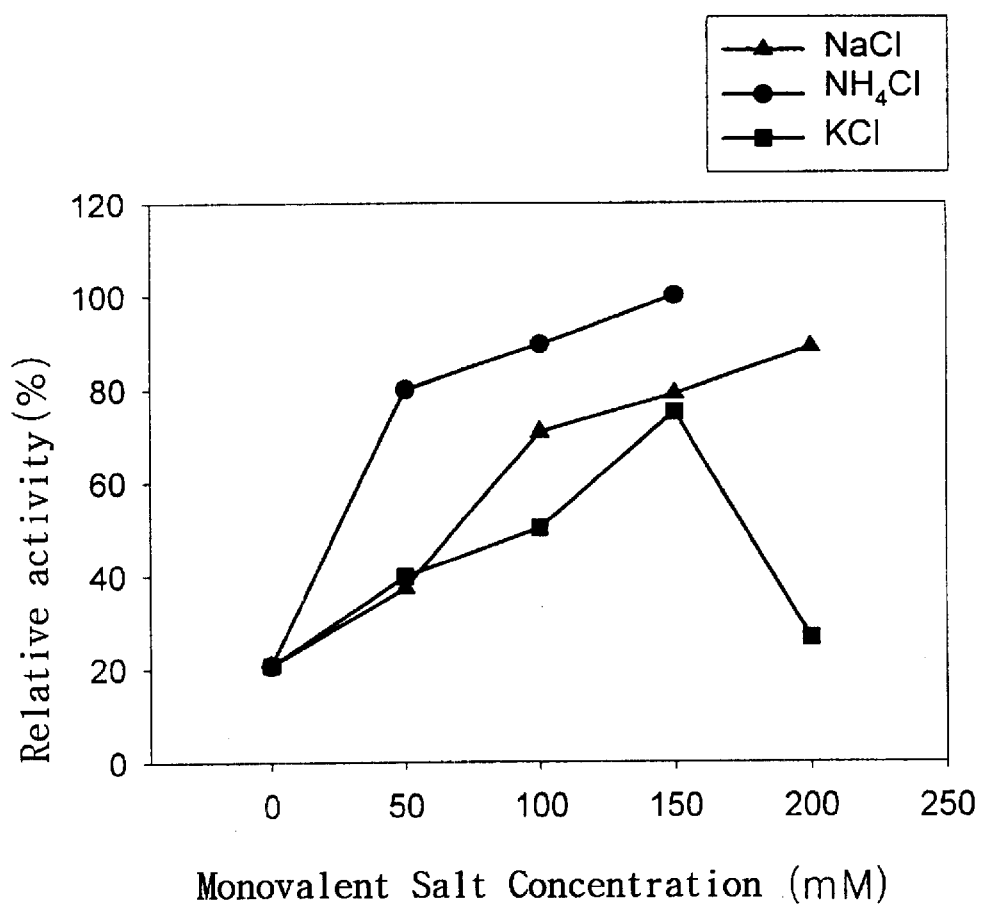
FIG. 6 is a graph showing DNA ligase activity according to ion concentration.

To determine the activity change of *Aquifex pyrophilus* DNA ligase according to a concentration and type of monovalent ion, each of monovalent salts, NaCl, KCl and $NH_4Cl$, were added to the reaction mixture. As a result, the activity of *Aquifex pyrophilus* DNA ligase gradually increased in proportion to the concentration of salt, up to 200 mM of NaCl, 150 mM of KCl, and 150 mM of $NH_4Cl$, respectively (FIG. 6a). However, the activity of the ligase decreased to a concentration above 150 mM of KCl.

Figure 6B:
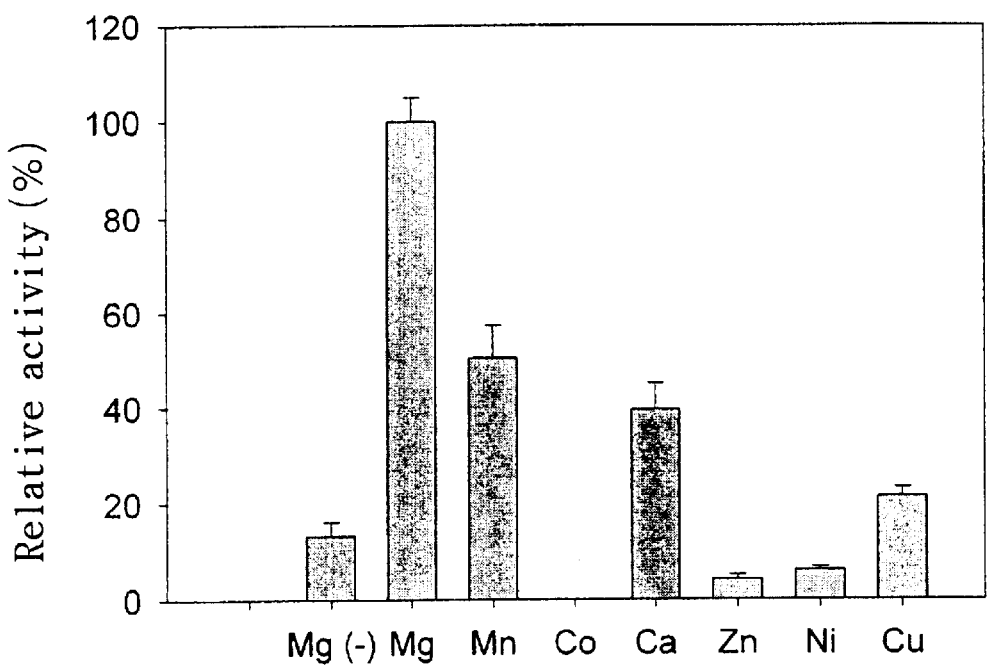

Divalent ions are essential for a ligation reaction. Most DNA ligases require the presence of $Mg^{2-}$ion. In order to determine the divalent ion specificity of *Aquifex pyrophilus* DNA ligase (1.2 pmol), the reaction solution (50 mM Tris-HCl, pH 8.0, 10 mM DTT, 5 mM $NaD^+$, 250 pmol of nick-containing oligonucleotide) was demetalized by using urea. Other divalent ions were added to the reaction mixture instead of $MgCl_2$. After reaction at 50° C. for 1 hour, relative activity of the enzyme was detected. All the used divalent ions were chlorides. *Aquifex pyrophilus* DNA ligase showed the highest activity at 10 mM $MgCl_2$. And 50% and 40% of the relative activity was observed at a concentration of not more than 5 mM in the cases of $Mn^{2+}$ and $Ca^{2-}$, respectively (FIG. 6b).

Figure 7A:
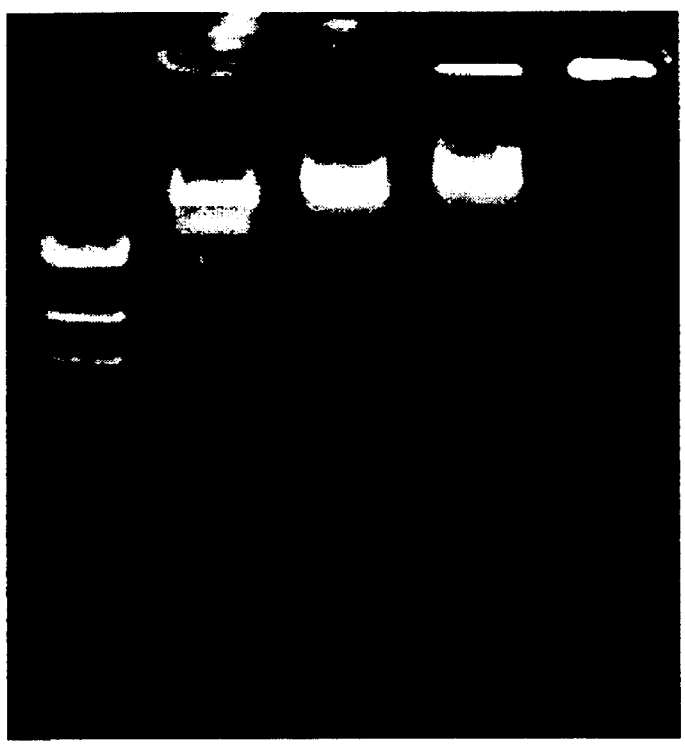
FIG. 7 is a graph showing DNA ligase activity with respect to temperature.

To determine the activity of *Aquifex pyrophilus* DNA ligase depending on the temperature, a ligation of HindIII-cleaved $\lambda$ DNA fragments by *Aquifex pyrophilus* DNA ligase was examined at the various temperatures of 37° C., 42° C., 50° C. and 65° C. The result showed that the activity of *Aquifex pyrophilus* DNA ligase increased up to 50° C. as the temperature increased (FIG. 7a).

Figure 7B:
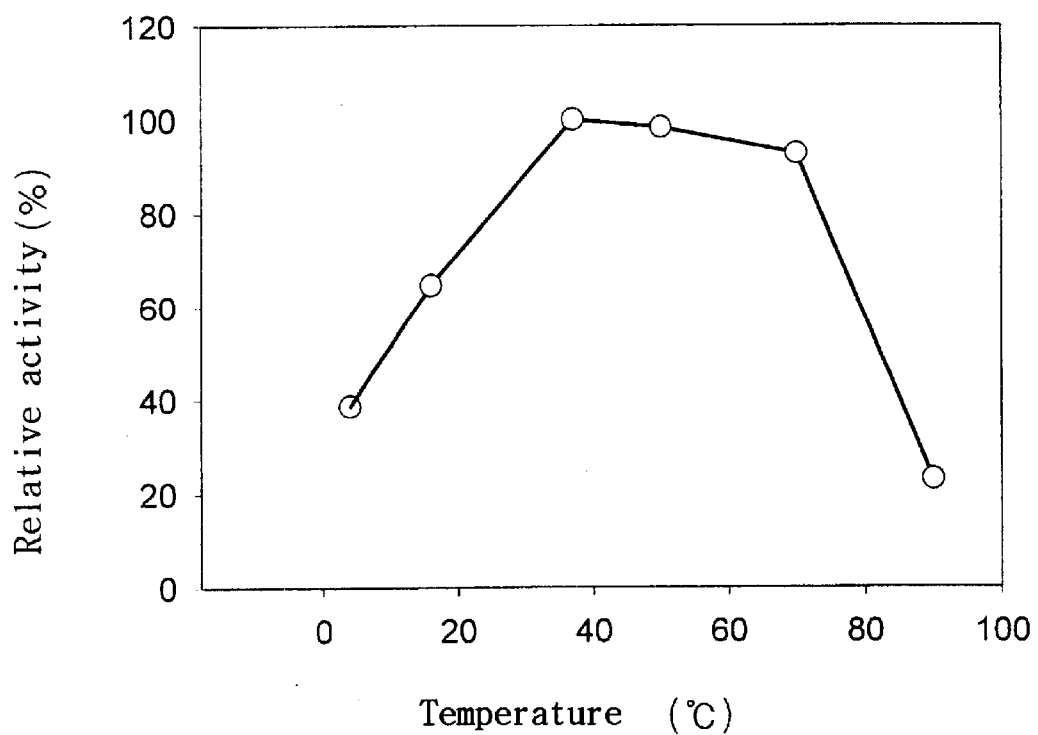

To study a nick ligation activity of *Aquifex pyrophilus* DNA ligase, a radioactive isotope-labeled oligo-duplex substrate (71mer) containing a nick was used for the reaction. The result indicated that the ligase showed the highest activity at 37° C. after reaction, and that the activity similar to the highest activity was shown at the optimum temperature of 37° C. to 75° C. (FIG. 7b).

EXAMPLE 4

Determination of Thermostability of DNA Ligase Protein

To measure a thermostability of the DNA ligase, the DNA ligase of *Aquifex pyrophilus* (0.1 mg/ml) was incubated in a buffer solution (50 mM Tris-HCl, pH 8.0, 10 mM DTT, 10 mM MgCl$_2$) at 95° C. Aliquots (25 ng) were taken at regular time intervals, immediately chilled on ice, and the activity of each aliquot was analyzed (FIG. 8). To compare the thermostability, the thermostability of *E. coli* DNA ligase and *Thermus aquifex* DNA ligase was also determined in the same manner as in *Aquifex pyrophilus*. It was identified that *Aquifex pyrophilus* DNA ligase has 75% of the ligation activity after heating at 95° C. for 1 hour while the half-lives of *E. coli* DNA ligase and *Thermus aquifex* DNA ligase were shown as 5 min and 2 min at 95° C., respectively. Therefore, it can be concluded that the *Aquifex pyrophilus* DNA ligase has superior thermostability to the ligase from *E. coli* and *Thermus aquifex*.

EXAMPLE 5

Application of *Aquifex pyrophilus* DNA Ligase to RED Assay

A thermostable ligase is essential for repeat expansion detection (RED) assay, which is used for diagnosing the genetic diseases that are caused by change of trinucleotide repeats in certain chromosome. In order to determine whether the DNA ligase of the present invention could be applied to RED, the activity of the DNA ligase according to the present invention was compared with that of the commercially available Ampligase by Epicentre, which is mostly used in RED.

A reaction mixture consisting of an amount of *Aquifex pyrophilus* DNA ligase, reaction buffer (50 mM Tris-HCl, pH 8.4, 10 mM MgCl$_2$, 1 mM NAD$^+$, 50 mM KCl and 0.1% Triton X-100), radioisotope-labeled oligonucleotide (CTG)$_{10}$, and human genomic DNA, which bears a few hundreds repeats of the CTG sequence, was prepared. The reaction was performed in a Thermal Cycler (Perkin-Elmer Co.) using the following conditions: 500 cycles of 30 minutes at 74° C., followed by 4 minutes at 96° C. The sample was analyzed by gel electrophoresis on 10% acrylamide gel and then on an autoradiogram.

In FIG. 9, the amount of *Aquifex pyrophilus* DNA ligase added to the ligation reaction is as follows: 1.2 pmol (lane 1), 2.4 pmol (lane 2), 3.6 pmol (lane 3), 4.8 pmol (lane 4), 6.1 pmol (lane 5). Lane 6 was the result shown by using 5U Ampligase for comparison. As shown in FIG. 9, it was understood that the DNA ligase of the present invention shows a higher activity than Ampligase so that the DNA ligase of the invention can be applied to RED more efficiently.

As seen above, *Aquifex pyrophilus* DNA ligase of the present invention has higher stability than DNA ligase from the preexisting bacteria under high temperatures so that it can be advantageously used in assay in a related medical field, etc.

---

What is claimed is:

1. An isolated gene coding for *Aquifex pyrophilus* DNA ligase having a base sequence of SEQ. ID. NO: 3.
2. Plasmid pLIG containing the gene coding for *Aquifex pyrophilus* DNA ligase according to claim 1.
3. *E. coli* BL21(DE3)/pSJS1240-pLig which is transformed with plasmid pLIG according to claim 2.
4. Probe consisting of a base sequence of SEQ. ID. NO: 1 or SEQ. ID. NO: 2.
5. Process for preparing *Aquifex pyrophilus* DNA ligase comprising the steps of: culturing *E. coli* BL21(DE3)/pSJS1240-pLig according to claim 3 inducing an expression of DNA ligase by adding IPTG in culture; and recovering and purifying the expressed DNA ligase.
6. *Aquifex pyrophilus* DNA ligase which is expressed from the *E. coli* according to claim 3.

* * * * *